United States Patent
Mishima et al.

(10) Patent No.: US 7,470,264 B2
(45) Date of Patent: Dec. 30, 2008

(54) DISPOSABLE ABSORBENT ARTICLE WITH POCKET FOR ISOLATING FECES FROM URINE

(75) Inventors: Yoshitaka Mishima, Mitoyo-gun (JP); Kaiyo Nakajima, Mitoyo-gun (JP)

(73) Assignee: Uni-Charm Corporation, Ehime-ken (JP)

( * ) Notice: Subject to any disclaimer, the term of this patent is extended or adjusted under 35 U.S.C. 154(b) by 240 days.

(21) Appl. No.: 11/074,644

(22) Filed: Mar. 9, 2005

(65) Prior Publication Data

US 2005/0203477 A1    Sep. 15, 2005

(30) Foreign Application Priority Data

Mar. 12, 2004  (JP) .............................. 2004-070345

(51) Int. Cl.
*A61F 13/15*  (2006.01)
*A61F 13/20*  (2006.01)

(52) U.S. Cl. ................ 604/385.101; 604/378; 604/385.01

(58) Field of Classification Search ............ 604/385.19, 604/385.24–385.28, 385.101, 385.01
See application file for complete search history.

(56) References Cited

U.S. PATENT DOCUMENTS

| | | | |
|---|---|---|---|
| 5,558,661 A | | 9/1996 | Roe et al. |
| 5,667,503 A | * | 9/1997 | Roe et al. ............... 604/385.19 |
| 6,165,160 A | | 12/2000 | Suzuki et al. |
| 6,248,098 B1 | * | 6/2001 | Sayama .................. 604/385.28 |
| 6,383,170 B1 | * | 5/2002 | Mishima et al. ........ 604/385.19 |
| 6,406,465 B1 | | 6/2002 | Otsubo |
| 6,638,260 B2 | * | 10/2003 | Mishima ................ 604/385.01 |
| 2001/0016719 A1 | | 8/2001 | Mishima |
| 2002/0077615 A1 | | 6/2002 | Mishima |

FOREIGN PATENT DOCUMENTS

| | | |
|---|---|---|
| EP | 0955028 | 11/1999 |
| EP | 1 114 631 A2 | 7/2001 |
| EP | 1 234 563 A3 | 8/2002 |
| EP | 1 323 399 A2 | 7/2003 |
| JP | 1996-196565 | 8/1996 |
| JP | 1 224 922 A3 | 11/2003 |
| JP | 2002-325563 A | 11/2003 |
| WO | WO 9963921 A1 * | 12/1999 |

* cited by examiner

*Primary Examiner*—Michele Kidwell
(74) *Attorney, Agent, or Firm*—Lowe Hauptman Ham & Berner, LLP

(57) ABSTRACT

A disposable wearing article includes a liquid-impervious chassis, a body fluid absorbent first panel extending over a crotch region and a rear waist region of the chassis and a body fluid absorbent second panel extending over a front waist region and the crotch region of the chassis. The second panel has a front portion joined to the front waist region, a distal portion lying above the crotch region and transversely opposite side edges joined to transversely opposite lateral sections of the chassis. The distal portion is spaced apart upward from the chassis and thereby a pocket opening from the crotch region toward the rear waist region is formed between the chassis and the distal portion of the second panel.

15 Claims, 16 Drawing Sheets

DISPOSABLE ABSORBENT ARTICLE WITH POCKET FOR ISOLATING FECES FROM URINE

RELATED APPLICATIONS

The present application is based on, and claims priority from, Japanese Application Serial Number 2004-70345, filed Mar. 12, 2004, the disclosure of which is hereby incorporated by reference herein in its entirety.

BACKGROUND OF THE INVENTION

The present invention relates to a disposable wearing article adapted for absorption and retention of bodily wastes.

There has already been proposed a disposable diaper having a front waist region, a rear waist region and a crotch region extending between these waist regions and comprising a liquid-pervious topsheet facing the wearer, a liquid-impervious backsheet facing away from the wearer and a liquid-absorbent core interposed between these top- and backsheets and extending between the front and rear waist regions. The core consists of an upper layer core and a lower layer core overlapping each other in a thickness direction of the diaper. Such a diaper is disclosed, for example, in Japanese Unexamined Patent Application Publication No. 1996-196565 (hereinafter referred to as "Citation").

The upper layer core comprises, in turn, a front core extending from the front waist region into the crotch region and a rear core extending from the crotch region into the rear waist region. Ends of the front and rear cores facing each other are spaced in a back-and-forth direction by a predetermined dimension. Between these ends of the front and rear cores facing each other, the lower layer core covered with the topsheet is exposed. The topsheet covering the upper surface of the upper layer core are folded downward toward the lower layer core along the respective ends of the front and rear cores facing each other, the lower layer core covered with the topsheet is exposed. The topsheet covering the upper surface of the upper layer core are folded downward toward the lower layer core along the respective ends of the front and rear cores facing each other and folded into a space defined between the upper layer core and the lower layer core. In this diaper of prior art, difference in level between is defined between the front and rear cores, i.e., the upper layer core and the lower layer core in the crotch region so that the ends of the front and rear cores facing each other may cooperate with the lower layer core to form a pocket depressed in a thickness direction of the diaper.

In the case of the diaper disclosed in Citation, however, respective lower surfaces of the front and rear cores readily come in contact with the upper surface of the lower layer core and it is difficult for this known diaper to form a desired space between the front core and the lower layer core as sell as to form a desired space between the rear core and the lower layer core. Even if bodily wastes moves into the pocket formed in the crotch region, body wastes can not be properly received between the front core and the lower layer core as well as between the rear core and the lower layer core. Even if a limited space is formed between the front and rear cores and the lower layer core, it is impossible for such limited space to accommodate a large amount of bodily waste which rather spreads over a wide section of the upper surfaces of the front and rear cores and/or the lower layer core. Consequently, urine and feces of bodily wastes may be mixed with each other and the wearer's skin may be contaminated with such a mixture. Furthermore, the upper layer core and the lower layer core are placed upon each other in the front and rear waist regions and thickness dimensions of the core in the front and rear waist regions are unacceptably increased to make the core bulky in these waist regions. Such a bulkiness may create a feeling of discomfort against the wearer.

SUMMARY OF THE INVENTION

It is an object of the present invention to provide a disposable wearing article improved so that the crotch region can be formed with a pocket adapted to receive feces without being mixed with urine, on one hand, and the wearer can be free from a feeling of discomfort due to local bulkiness of the core, on the other hand.

According to the present invention, there is provided a disposable wearing article having longitudinal and transverse direction, comprising: a liquid-impervious chassis having an inner surface, a front waist region, a rear waist region, a crotch region extending therebetween, front and rear ends respectively extending a cross the front and rear waist regions in the transverse direction and opposite lateral sections extending in the longitudinal direction between the front and rear ends; a body fluid absorbent first panel having a front portion, a rear portion and opposite side edges and laid on the inner surface of the chassis so as to extend over the rear waist region and the crotch region of the chassis.

The article further comprises a body fluid absorbent second panel having a proximal portion, a distal portion and opposite side edges and laid on the inner surface of the chassis so as to extend over the front waist region and the crotch region of the chassis; the first panel being fixed at least at the front and rear portions to the chassis while the second panel being fixed at least at the proximal portion to the front end of the front waist region of the chassis, the distal portion extending over the crotch region of the chassis and the opposite side edges extending along the opposite lateral sections of the chassis; and the distal portion of the second panel being spaced apart from the chassis, with the distal portion being bent upward at a predetermined angle with respect the chassis, along a zone contiguous to the proximal portion, to form between the chassis and the distal portion with a pocket opening from the crotch region toward the rear waist region.

The present invention may include the following preferred embodiments.

The front portion of the first panel extends to at least a generally front half of the crotch region while the distal portion of the second panel extends to a generally front half of the crotch region and at least of the front portion of the first panel underlies the distal portion of the second panel and extends into the pocket.

A pocket is provided with a spacer extending in the transverse direction. The spacer has transversely opposite ends joined to at least one of the transversely opposite lateral sections of the chassis and transversely opposite lateral portions of the distal portion of the second panel and an intermediate section defined between the transversely opposite ends. According to this embodiment, the transversely opposite lateral sections of the distal portion are drawn by the spacer inward as viewed in the transverse direction of the chassis.

The spacer is elastically stretchable in the transverse direction and contractibly attached to the pocket. The spacer has transversely opposite ends joined to at least one of the transversely opposite lateral sections of the chassis and transversely opposite lateral portions of the distal portion of the second panel and an intermediate section defined between the transversely opposite ends. According to this embodiment, the transversely opposite lateral sections of the distal portion are drawn inward as viewed in the transverse direction of the chassis under contractile force of the spacer.

The wearing article further includes a pair of liquid-impervious leak-barrier sheets respectively laid on the lateral sections of the chassis and extending in the longitudinal direction. The leak-barrier sheets respectively have lateral sections extending in the longitudinal direction along the lateral sections of the chassis, distal sections extending in parallel to side edges of the lateral sections in the longitudinal direction and normally biased to rise above the chassis and longitudinally opposite ends lying on the front and rear ends and collapsed in the transverse direction of the chassis. According to this embodiment, the first and second panels lie between the distal sections of the leak-barrier sheets and the distal portions of the second panel have the lateral sections connected with the distal sections of the leak-barrier sheets.

The distal sections of the leak-barrier sheet respectively have distal edges to which stretchable elastic members extending in the longitudinal direction are contractibly attached. According to this embodiment, the distal portion of the second panel has the transversely opposite lateral sections connected with the distal sections of the leak-barrier sheets below the distal edges and an apex of the intermediate section of the distal portion lies at a level above the distal edges.

A pair of folding guides spaced from each other by a predetermined dimension in the transverse direction and extending in a generally longitudinal direction are formed between the transversely opposite lateral sections and the middle section of the distal portion of the second panel.

The distal portion of the second panel has the transversely opposite lateral sections connected with the distal sections of the leak-barrier sheet in a vicinity of the folding guides.

The folding guides obliquely extend from the distal portion to the transversely opposite side edges of the second panel.

The second panel presents a stiffness lower along the folding guides than in the distal portion of the second panel except for the folding guides.

The second panel has a stiffness higher along the folding guides than in the distal portion of the second panel except for the folding guides.

The first panel comprises a liquid-pervious first sheet and a liquid-absorbent first core underlying the first sheet while the second panel comprises a liquid-pervious second sheet and a liquid-absorbent second core wrapped with the second sheet.

With the article according to the present invention, the distal portion of the second panel rises in an upward convex circular arc above the chassis and, between the chassis and the distal portion, the pocket opening from the crotch region toward the rear waist region is formed. In this way, the pocket reliably receives feces even if feces discharged onto the rear half of the crotch region and the rear waist region moves toward the front waist region. Urine discharged onto the front waist region and the crotch region is absorbed and contained by the second panel while feces discharged onto the crotch region and the rear waist region is absorbed and contained by the first panel and then received by the pocket. In this way, urine and feces are separated from each other and thus the wearer's skin is reliably protected from being contaminated with a mixture of urine and feces. Furthermore it is unlikely that the first and second panels might overlap each other in the front and rear waist regions to make these panels locally bulky and the wearer of the article might suffer from a feeling of discomfort.

With the embodiment of the invention wherein the front portion of the first panel extends over a generally front half of the crotch region while the distal portion of the second panel extends over a generally front half of the crotch region and a front end of the front portion of the first panel underlies the distal portion of the second panel and extends into the pocket, the pocket is formed over a generally front half of the crotch region starting from a vicinity of a longitudinally middle section of the crotch region and urine discharged onto the front waist region and the crotch region is absorbed and contained by the second panel while feces discharged onto the crotch region and the rear waist region is absorbed and contained by the first panel and then received by the pocket. The distal portion of the second panel is positioned between the genital organ and the anus of the wearer, so urine and feces can be reliably separated from each other and the wearer can be reliably protected from contamination due to a mixture of urine and feces. The front portion of the first panel has the distal section underlying the distal portion of the second panel and extending into the pocket. Such an arrangement allows urine as well as feces to be absorbed and contained by the core of the first panel in the pocket and thereby prevents urine and feces from being mixed with each other even if urine permeate the second panel into the pocket.

With the embodiment of the invention wherein the pocket is provided with the spacer extending in the transverse direction and the transversely opposite lateral sections of the distal portion of the second panel are drawn by the spacer inward as viewed in the transverse direction of the chassis, the shape of the distal portion is kept by the spacer convex upward above the chassis and it is unlikely that the transversely opposite lateral sections extending upward above the chassis might be unintentionally collapsed. In this way, the spacer can be effectively utilized to reliably keep the shape of the pocket formed between the chassis and the distal portions of the second panel. The pocket is hard to be closed and can reliably receive feces.

With the embodiment of the invention wherein the spacer is elastically stretchable in the transverse direction and contractibly attached to the pocket so that the transversely opposite lateral sections of the distal portion are drawn inward as viewed in the transverse direction of the chassis under contractile force of the spacer, the shape of the distal portion is kept by the spacer convex upward above the chassis and it is unlikely that the transversely opposite lateral sections extending upward above the chassis might be unintentionally collapsed. In this way, the spacer can be effectively utilized to reliably keep the shape of the pocket formed between the chassis and the distal portions of the second panel. The pocket is hard to be closed and can reliably receive feces.

With the embodiment of the invention wherein the article includes a pair of liquid-impervious leak-barrier sheets respectively laid on the lateral sections of the chassis and extending in the longitudinal direction wherein the side edges of the distal portion of the second panel are connected with the distal sections of the respective leak-barrier sheets, the distal portion of the second panel is raised above the chassis by the distal sections of the respective leak-barrier sheets and thereby the shape of the distal portion of the second panel is kept convex upward above the chassis and it is unlikely that the transversely opposite lateral sections extending upward above the chassis might be unintentionally collapsed. In this way, the spacer can be effectively utilized to reliably keep the shape of the pocket formed between the chassis and the distal portions of the second panel. The pocket is hard to be closed and can reliably receive feces.

With the embodiment of the invention wherein the distal sections of the leak-barrier sheet respectively have distal edges to which the transversely opposite lateral sections of the distal portion of the second panel are connected with the distal sections of the respective leak-barrier sheets below the distal edges and the apex of the intermediate section of the distal portion lies at a level above the distal edges, the distal edges of the distal sections of the second panel form the barriers against urine adapted to prevent movement of urine even if urine spreadings over the upper surface of the distal portion of the second panel moves toward the lateral sections of the distal portion. These barriers prevent urine from leaking sideways beyond the lateral sections of the distal portion. The apex of the intermediate section of the distal portion lies above the distal edges and therefore the apex of the intermediate comes in contact with the wearer's crotch region ahead of the distal edges. Consequentially, it is unlikely that the distal edges might be collapsed in the transverse direction of the article and the function of these distal edges as the barriers against urine might be disabled.

With the embodiment of the invention wherein a pair of folding guides spaced from each other by a predetermined dimension in the transverse direction and extending in a generally longitudinal direction are formed between the transversely opposite lateral sections and the middle section of the distal portion of the second panel, the distal portion is folded along these folding guides and the lateral sections of the distal portion extending outside these folding guides are facilitated to rise above the chassis. In this way, the pocket can be reliably formed between the chassis and the distal portion of the second panel.

With the embodiment of the invention wherein the folding guides obliquely extend from the distal portion to the opposite side edges of the second panel, the distal portion of the second panel is distinctly divided into the transversely opposite lateral sections defined outside the respective folding guides and the intermediate section defined between the pair of folding guides. In this way, the lateral sections defined outside the respective folding guides may be facilitated to rise above the chassis. Consequentially, the opposite lateral sections defined outside the respective folding guides are thereby facilitated to rise above the chassis and the distal portion of the second panel is facilitate to be convex upward above the chassis. In this manner, the pocket can be reliably formed between the chassis and the distal portion of the second panel.

With the embodiment of the invention wherein the second panel has a stiffness lower along the folding guides than in the distal portion of the second panel except for the folding guides, the distal portion can be reliably folded along the folding guides and thereby the distal portion of the second panel can easily become convex upward above the chassis. In this way, the pocket can be reliably formed between the chassis and the distal portion of the second panel.

With the embodiment of the invention wherein the second panel has a stiffness higher along the folding guides than in the distal portion of the second panel except for the folding guides, the distal portion can be reliably folded on both sides of each of the folding guides and thereby the distal portion of the second panel can easily become convex upward above the chassis. In this way, the pocket can be reliably formed between the chassis and the distal portion of the second panel.

With the embodiment of the invention wherein the first panel comprises a liquid-pervious first sheet and a liquid-absorbent first core underlying the first sheet while the second panel comprises a liquid-pervious second sheet and a liquid-absorbent second core wrapped with the second sheet, urine is absorbed and retained by the second core while feces is absorbed and retained by the first core. In this way, it is not apprehended that urine and feces might leak from the first and second panels.

DETAILED DESCRIPTION OF THE PREFERRED EMBODIMENTS

Details of the disposable wearing article according to the present invention will be more fully understood from the description of an open-type disposable diaper as a typical embodiment given hereunder with reference to the accompanying drawings.

Figure 1:
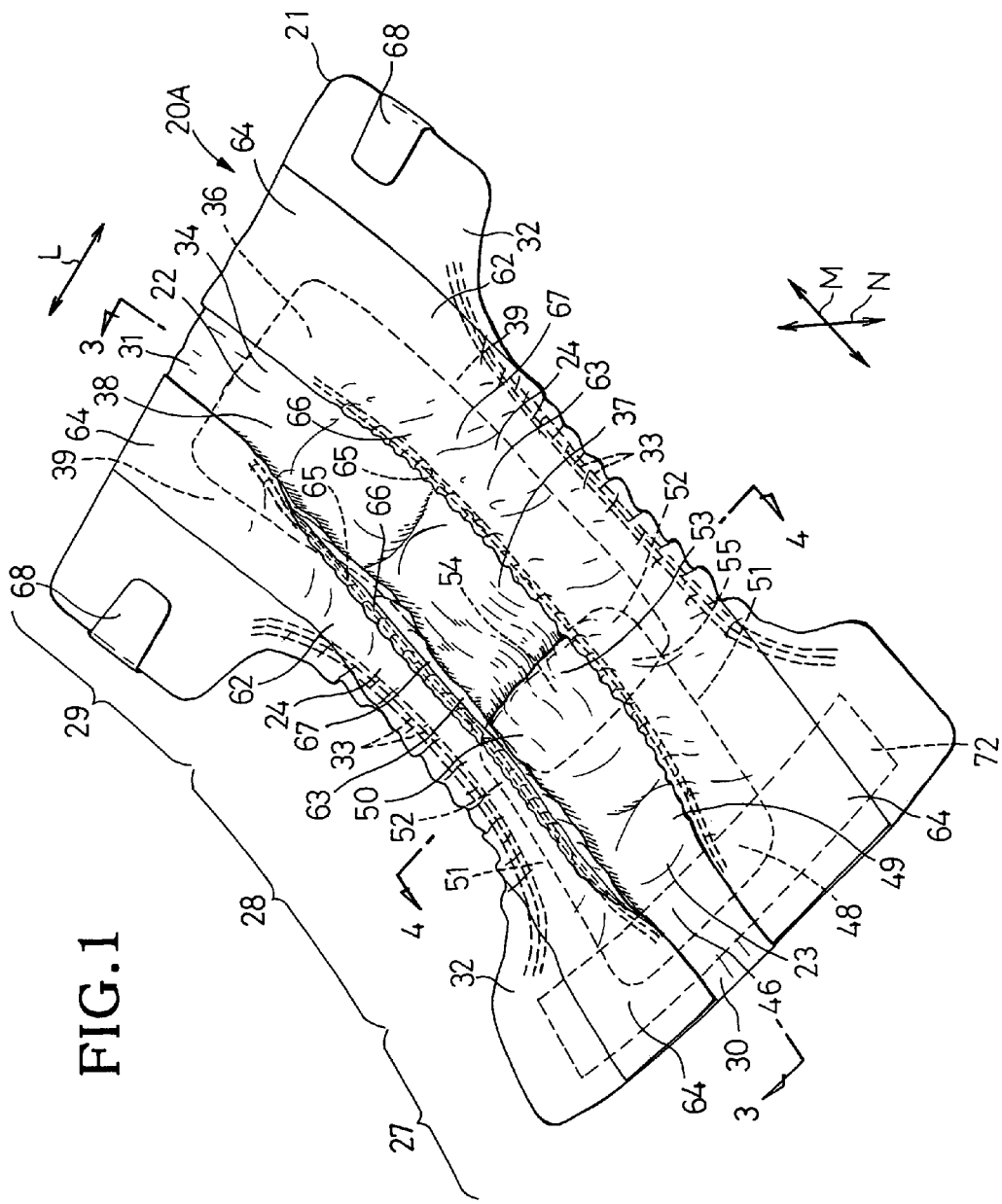
FIG. 1 is a perspective view showing a disposable diaper according to a typical embodiment of the invention.
Figure 2:
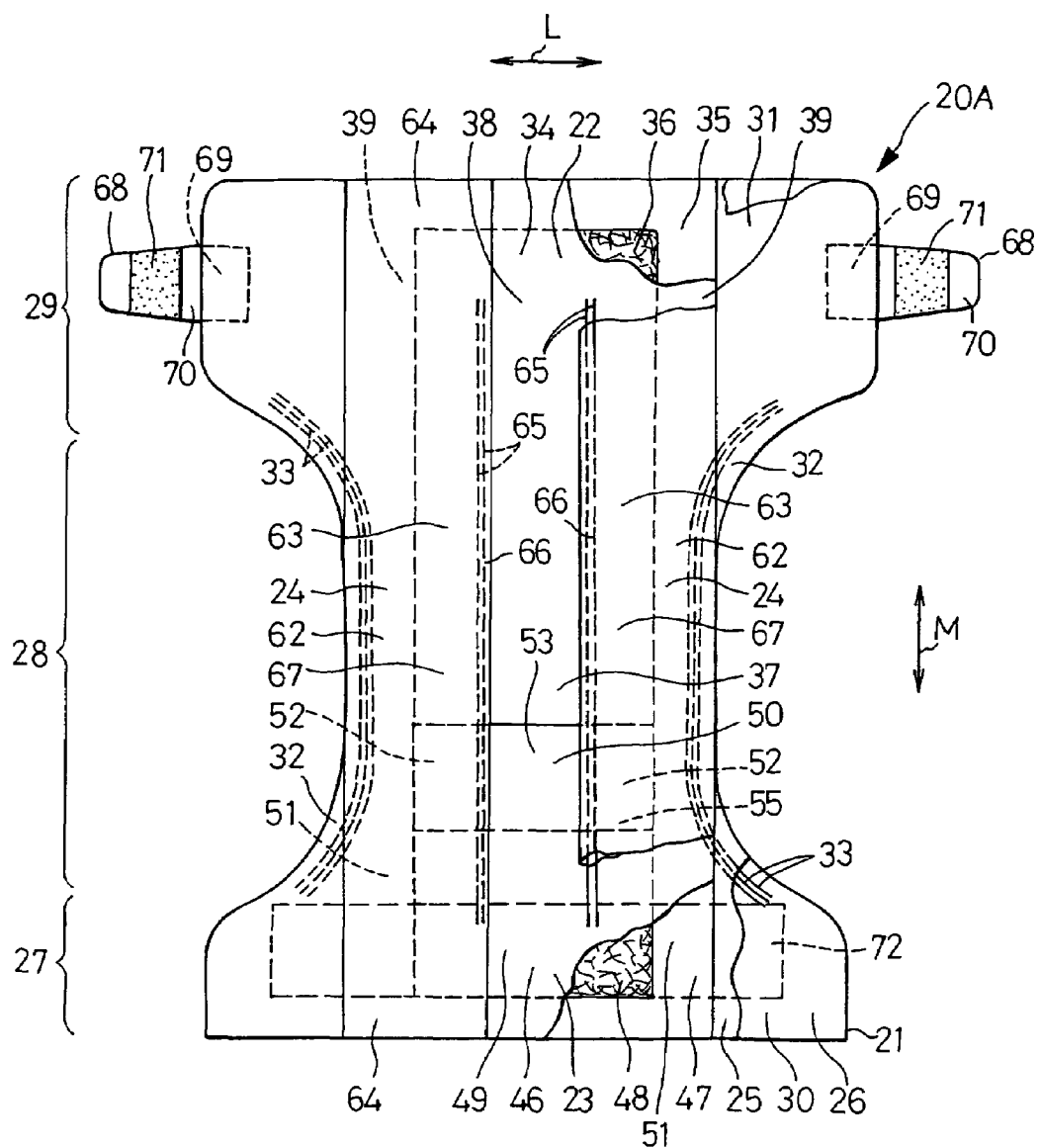
FIG. 2 is a partially cutaway plan view showing the diaper of FIG. 1 as viewed from the side of the panel.
Figure 3:
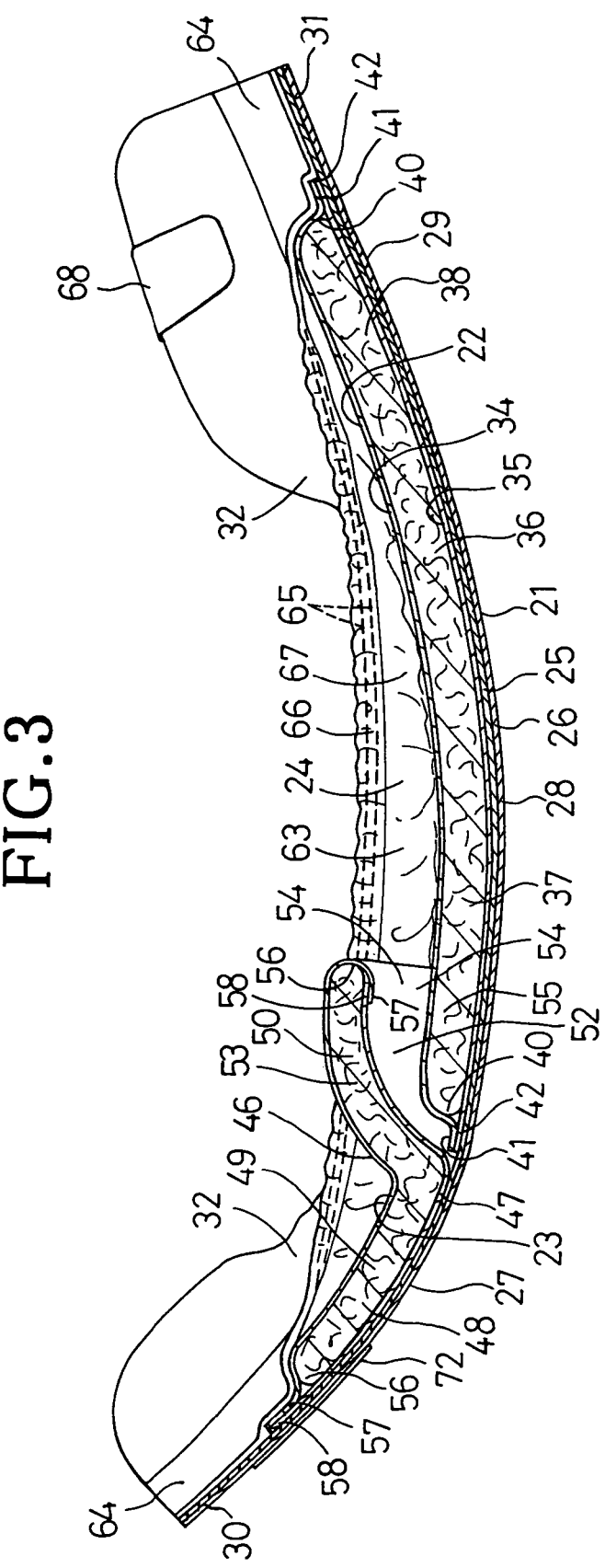
FIG. 3 is a sectional view taken along the line 3-3 in FIG. 1.
Figure 4:
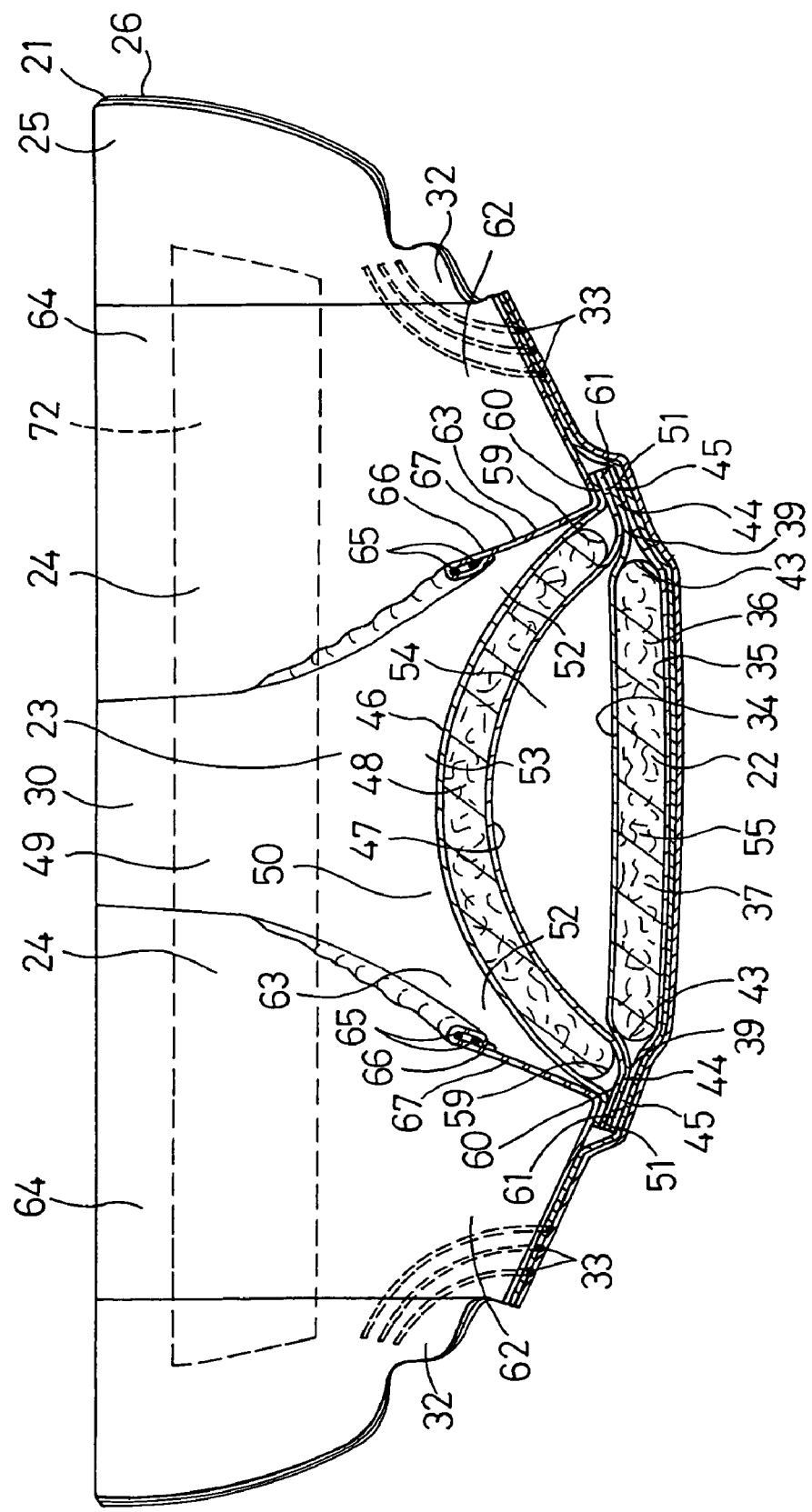
FIG. 4 is a sectional view taken along the line 4-4 in FIG. 1.

FIG. 1 is a perspective view showing a disposable diaper 20A according to a typical embodiment of the invention, FIG. 2 is a partially cutaway plan view showing the diaper 20A of FIG. 1 as viewed from the side of first and second panels 22, 23, FIG. 3 is a sectional view taken along the line 3-3 in FIG. 1 and FIG. 4 is a sectional view taken along the line 4-4 in FIG. 1. In FIGS. 1 and 2, a transverse direction is indicated by an arrow L, a longitudinal direction is indicated by an arrow M and a thickness direction is indicated by an arrow N (in FIG. 1 alone). FIG. 2 shows the diaper 20A as developed against a contractile force of elastic members 33, 65 in the longitudinal direction as well as in the transverse direction.

The diaper 20A comprises a liquid-impervious chassis 21 and first and second body fluid absorbent panels 22, 23 laid back and forth in the longitudinal direction on the inner side of the chassis 21. The diaper 20A further comprises a pair of liquid-impervious leak-barrier sheets 24 extending in the longitudinal direction on the inner side of the chassis 21.

The chassis 21 is formed of a composite sheet consisting of a hydrophobic fibrous nonwoven fabric 25 facing the wearer's skin and a breathable liquid-impervious plastic film 26 facing away from the wearer's skin laminated together wherein mutually opposed surfaces of these nonwoven fabric 25 and film 26 are joined to each other. The chassis 21 defines, in the longitudinal direction, a front waist region 27, a rear waist region 29 and a crotch region 28 extending between these waist regions 27, 29. The chassis 21 is contoured by front and rear ends 30, 31 respectively extending across the front and rear waist regions 27, 29 in the transverse direction and transversely opposite lateral sections 32 extending in the longitudinal direction between the front and rear waist regions 27, 29. In the crotch region 28, these lateral sections 32 describe circular arcs which are convex inward as viewed in the transverse direction of the chassis 21 to form the diaper 1A into a generally hourglass-like shape. A plurality of leg-surrounding elastic members 33 extending along the respective lateral sections 32 of the crotch region 28 are contractibly attached to the chassis 21. The leg-surrounding elastic members 33 are interposed between the nonwoven fabric 25 and the film 26 and joined to mutually opposed surfaces of these nonwoven fabric 25 and film 26 while the elastic members 33 are stretched at a predetermined ratio in the longitudinal direction.

The first panel 22 is shaped in a rectangle which is relatively long in the longitudinal direction and laid between respective distal sections 63 of the leak-barrier sheets 24 as will be described later so as to occupy the crotch region 28 and the rear waist region 29 of the chassis 21. The first panel 22 comprises a liquid-pervious sheet 34 (liquid-pervious first sheet) facing the wearer, a liquid-impervious sheet 35 facing away from the wearer and a liquid-absorbent core 36 (liquid-absorbent first core) interposed between the liquid-pervious sheet 34 and the liquid-impervious sheet 35 and joined to respective inner surfaces of these sheets 34, 35. The core 36 has its upper surface entirely covered with the liquid-pervious sheet 34 and its lower surface entirely covered with the liquid-impervious sheet 35.

The first panel 22 has a front portion 37 joined to the crotch region 28 of the chassis 21, a rear portion 38 joined to the rear waist region 29 of the chassis 21 and transversely opposite side edges 39 joined to the respective lateral sections 32 of the chassis 21. The front and rear portions 37, 38 are formed from the sheets 34, 35 and the core 36. The transversely opposite side edges 39 are formed from portions of the sheets 34, 35 overlapped together. Along the front and rear portions 37, 38 and the transversely opposite side edges 39, the liquid-impervious sheet 35 is joined to the chassis 21. The front portion 37 extends from the side of the rear waist region 29 toward the side of the front waist region 27 so as to be laid over at least a generally front half of the crotch region 28. The rear portion 38 is laid over a generally front half of the rear waist region 29 of the chassis 21.

In the first panel 22, longitudinally opposite ends 41, 42 of the sheets 34, 35 extend outward in the longitudinal direction beyond longitudinally opposite ends 40 of the core 36 and transversely opposite side edge portions 44, 45 of the sheets 34, 35 extend outward in the transverse direction beyond transversely opposite side edges 43 of the core 36. The respective ends 41, 42 of these sheets 34, 35 are overlapped together and have respective inner surfaces joined together while the respective side edge portions 44, 45 of these sheets 34, 35 are overlapped together and have respective inner surfaces joined together.

The second panel 23 is shaped in a rectangle which is relatively long in the longitudinal direction and laid between the respective distal sections 63 of the leak-barrier sheets 24 so as to occupy the front waist region 27 and the crotch region 28 of the chassis 21. The second panel 23 comprises a liquid-pervious sheet 46 (liquid-pervious second sheet) facing the wearer, a liquid-pervious sheet 47 (liquid-pervious second sheet) facing away from the wearer and a liquid-absorbent core 48 (liquid-absorbent first core) interposed between the liquid-pervious sheets 46, 47 and joined to respective inner surfaces of these sheets 46, 47. The core 48 has its upper surface entirely covered with the liquid-pervious sheet 46 and its lower surface entirely covered with the liquid-pervious sheet 47.

The second panel 23 has a front portion 49 joined to the front waist region 27 of the chassis 21, a distal portion 50 lying in the crotch region 28 of the chassis 21 and transversely opposite side edges 51 (transversely opposite side edges) joined to the respective lateral sections 32 of the chassis 21. The front and distal portions 49, 50 are formed from the sheets 46, 47 and the core 48. The transversely opposite side edges 51 are formed from portions of the sheets 46, 47 overlapped together. Along the front portion 49 and the transversely opposite side edges 51, the liquid-impervious sheet 47 is joined to the chassis 21. The front portion 49 extends from the side of the front waist region 27 toward the side of the rear waist region 29 so as to occupy a generally front half of the crotch region 28. The distal portion 50 is laid over a generally front half of the front waist region 27 of the chassis 21 and left free from the chassis 21.

The distal portion 50 of the second panel 23 comprises a pair of transverse opposite lateral sections 52 laid on the respective lateral sections 32 of the chassis 21 and an intermediate section 53 defined between the lateral sections 52. The lateral sections 52 and the intermediate section 53 are formed from the sheets 46, 47 and the core 48. The lateral sections 52 and the intermediate section 53 extends upward from the chassis 21 so as to describe a circular arc which is convex above the chassis 21. Specifically, the distal portion 50 is spaced apart from the chassis 21, with the distal portion being bent upward at a predetermined angle, preferably about 5 to about 60.degree., more preferably about 15 to about 45.degree., with respect to the chassis 21, along a bending zone 23a contiguous to the proximal portion. The bending zone 23a may be defined by embossing therealong. Alternatively, the distal portion may be convexed upward by drawing the transversely opposite lateral sections 52 so as to approach to each other and by bonding them on the chassis 21 in a convexed state thereof. A pocket 54 opening from the crotch region 28 toward the rear waist region 29 is formed between the chassis 21 and the distal portion 50 of the second panel 23. More specifically, the pocket 54 extends over a generally front half of the crotch region 28 starting from the vicinity of a longitudinally middle section of the crotch region 28. Below the distal portion 50 of the second panel 23, a front end 55 of the front portion 37 of the first panel 22 extends into the pocket 54.

In the second panel 23, longitudinally opposite ends 57, 58 of the sheets 46, 47 extend outward in the longitudinal direction beyond longitudinally opposite ends 56 of the core 48 and transversely opposite side edges 60, 61 of the sheets 46, 47 extend outward in the transverse direction beyond transversely opposite side edges 59 of the core 48. In the second panel 23, the respective ends 57, 58 of these sheets 46, 47 are overlapped together and have respective inner surfaces joined together while the respective side edges 60, 61 of these sheets 46, 47 are overlapped together and have respective inner surfaces joined together. In the distal portion 50, the respective ends 57, 58 of the sheets 46, 47 are folded toward the lower surface of the core 48.

The leak-barrier sheets 24 are laid on the respective lateral sections 32 of the chassis 21 and respectively comprise lateral portions 62 extending in the longitudinal direction, distal sections 63 extending in parallel to inner edges of the lateral portions 62 and normally biased to rise above the chassis 21 and longitudinally opposite ends 64 laid on the front and rear ends 30, 31, respectively, and collapsed inward as viewed in the transverse direction of the chassis 21. The lateral portions 62 and the distal sections 63 extend between the front and rear ends 30, 31 of the chassis 21. The distal sections 63 respectively have distal edges 66 along which stretchable elastic members 65 extending in the longitudinal direction are contractibly attached to the leak-barrier sheets 24 and middle sections 67 respectively extending from the distal edges 66 to the lateral portions 62. The elastic members 65 are secured to the respective distal edges 66 while these elastic members 65 are stretched at a predetermined ratio in the longitudinal direction. As the diaper 20A is curved with the inner surface of the chassis 21 inside and the elastic members 65 contract, the distal edges 66 correspondingly contract in the longitudinal direction and the distal sections 63 rise above the chassis 21 to form a pair of barriers against bodily wastes.

On the front end portion 30, the ends 64 of the respective leak-barrier sheets 24 have respective inner surfaces joined to the chassis 21 and the ends 57, 58 of the respective liquid-pervious sheets 46, 47 are interposed between the chassis 21 and the ends 64 of the respective leak-barrier sheets 24 and joined to inner and outer surfaces of these elements 21, 24. On the rear end portion 31, the ends 64 of the respective leak-barrier sheets 24 have respective inner surfaces joined to the chassis 21 and the ends of the liquid-pervious sheet 34 and the liquid-impervious sheet 35 are interposed between the chassis 21 and the ends 64 of the respective leak-barrier sheets 24 and joined to inner and outer surface of these elements 21, 24. Along the lateral sections 32, the lateral portions 62 of the respective leak-barrier sheets 24 have respective inner surfaces joined to the chassis 21 and the respective side edges 44, 45, 60, 61 of the liquid-pervious sheets 34, 46, 47 and the liquid-impervious sheet 35 are interposed between the chassis 21 and the lateral portions 62 of the respective leak-barrier sheets 24 and joined to inner and outer surfaces of these elements 21, 24.

The lateral sections 32 of the rear waist region 29 are respectively provided with a pair of flexible tape fasteners 68 comprising a fibrous nonwoven fabric. Each of these tape fasteners 68 has a proximal end portion 69 and a distal end portion 70 both extending in the transverse direction. The distal end portion 70 is interposed between the nonwoven fabric 25 and the film 26 and joined to mutually opposed surfaces of these nonwoven fabric 25 and film 26. The distal end portion 70 is provided on its inner surface with a hook member 71. The distal end portion 70 is folded inward as viewed in the transverse direction of the diaper 20A and temporarily anchored on the nonwoven fabric 25 of the chassis 21 by means of the hook member 71. It is possible without departing from the scope of the invention to replace the hook member 71 by a pressure-sensitive adhesive applied on the distal end portion 70.

The front waist region 27 is provided with a flexible target tape strip 72 on which the distal end portion 70 of the tape fastener 68 is to be detachably anchored. The target tape strip 72 is shaped in a rectangle which is relatively long in the transverse direction and comprises a loop member consisting of a fibrous chassis and loop elements from projecting the chassis (not shown). More specifically, the target tape strip 72 is joined to the outer surface of the chassis 21. When it is desired to coat the distal end portion 70 of the tape fastener 68 with a pressure-sensitive adhesive, a plastic film may be used as material for the target tape strip 72.

To put the diaper 20A on the wearer, the lateral sections 32 of the rear waist region 29 are placed upon the respective outer sides of the lateral sections 32 of the front waist region 27 and then the distal end portions 70 of the respective tape fasteners 68 are anchored on the target tape strip 72 by means of the respective hook members 71 to connect the front and rear waist regions 27, 29 with each other. Upon connection of the front and rear waist regions 27, 29 in this manner, the diaper 20A is formed with a waist-hole and a pair of leg-holes (not shown). Urine discharged onto the front waist region 27 and the front half of the crotch region 28 of the diaper 20A put on the wearer is absorbed and contained by the core 48 of the second panel 23 while moisture contained in feces discharged onto the rear half of the crotch region 28 and the rear waist region 29 is absorbed and contained by the core 36 of the first panel 22. Feces moving toward the front waist region 27 is received by the pocket 54. It is preferable that the second panel 23 is higher than the first panel 22 with respect to fluid absorption and fluid distribution characteristics so that urine may be rapidly absorbed.

The distal portion 50 of the second panel 23 rises above the chassis 21 and forms, between the chassis 21 and the distal 50, the pocket 54 opening from the crotch region 28 toward the rear waist region 29. In this way, the pocket 54 reliably receives feces even if feces discharged onto the rear half of the crotch region 28 and the rear waist region 29 moves toward the front waist region 27. Compared to the diaper according to the background art, the diaper 20A can receive a larger amount of feces.

In the diaper 20A, urine is absorbed and contained by the second panel 23 while feces is absorbed and contained by the first panel 22 and then received by the pocket 54. In this way, urine and feces are separated from each other and thus the wearer's skin is reliably protected from being contaminated with mixture of urine and feces. Furthermore it is unlikely that the first and second panels 22, 23 might overlap each other in the front and rear waist regions 27, 29 to make these panels 22, 23 locally bulky and the wearer of the diaper 20A might suffer from a feeling of discomfort.

The distal portion 50 of the second panel 23 is positioned between the genital organs and the anus of the wearer, so urine and feces can be reliably separated from each other and the wearer can be reliably protected from contamination due to a mixture of urine and feces. The front portion 37 of the first panel 22 has the distal section 55 underlying the distal portion 50 of the second panel 23 and extending into the pocket 54. Such an arrangement allows urine as well as feces to be absorbed and contained by the core 36 of the first panel 22 in the pocket 54 and thereby prevents urine and feces from being mixed with each other even if urine permeate the second panel into the pocket 54.

The barriers formed from the distal sections 63 of the respective leak-barrier sheets 24 against urine are effective to prevent urine from leaking sideways beyond the side edge portions of the chassis 21 even if urine spreadings on the respective upper surfaces (i.e., the upper surfaces of the liquid-pervious sheets 34, 46) of the first and second panels 22, 23 flows toward the side edges 39, 51.

Figure 5:
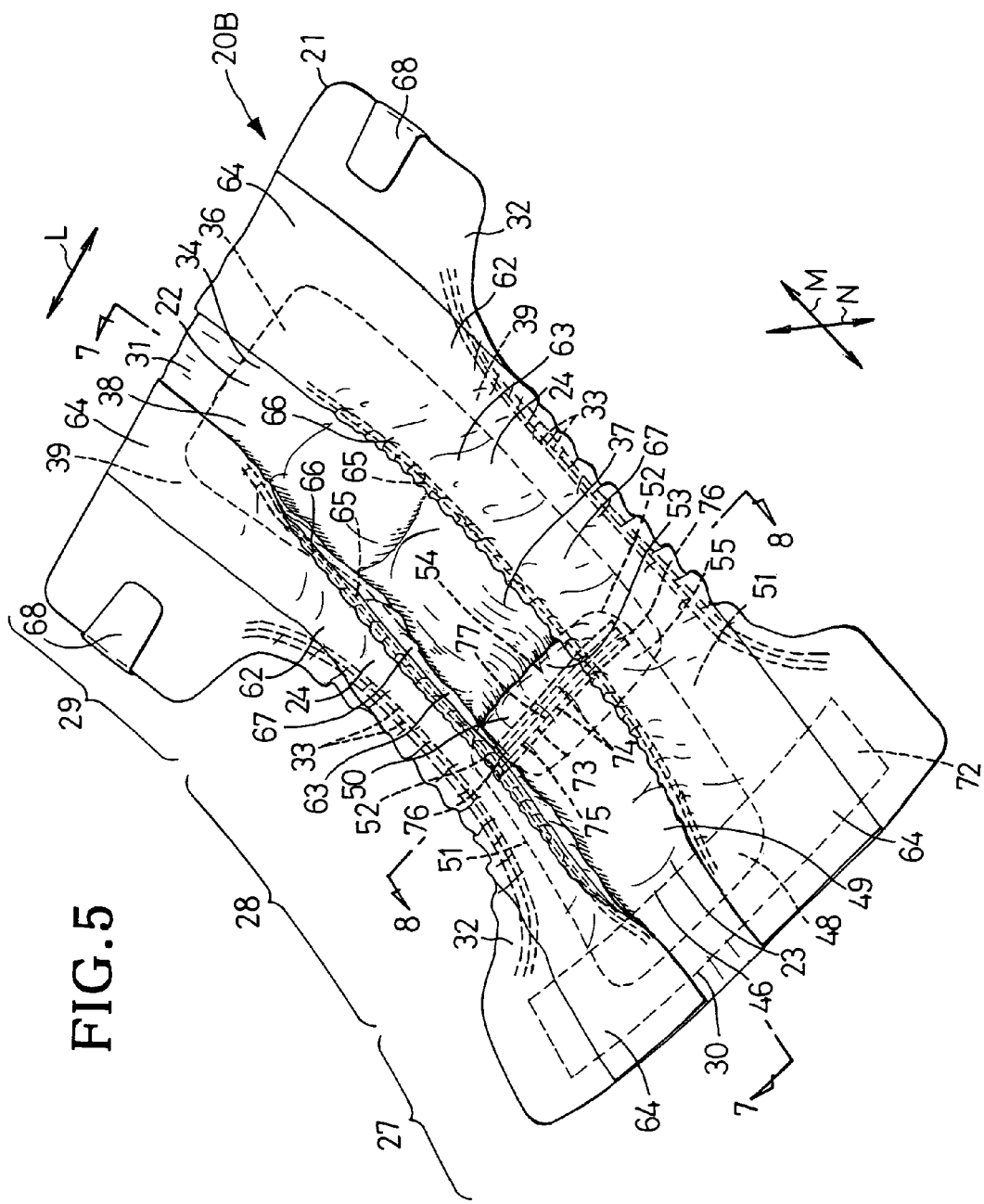
FIG. 5 is a perspective view showing a disposable diaper according to another embodiment of the invention.
Figure 6:
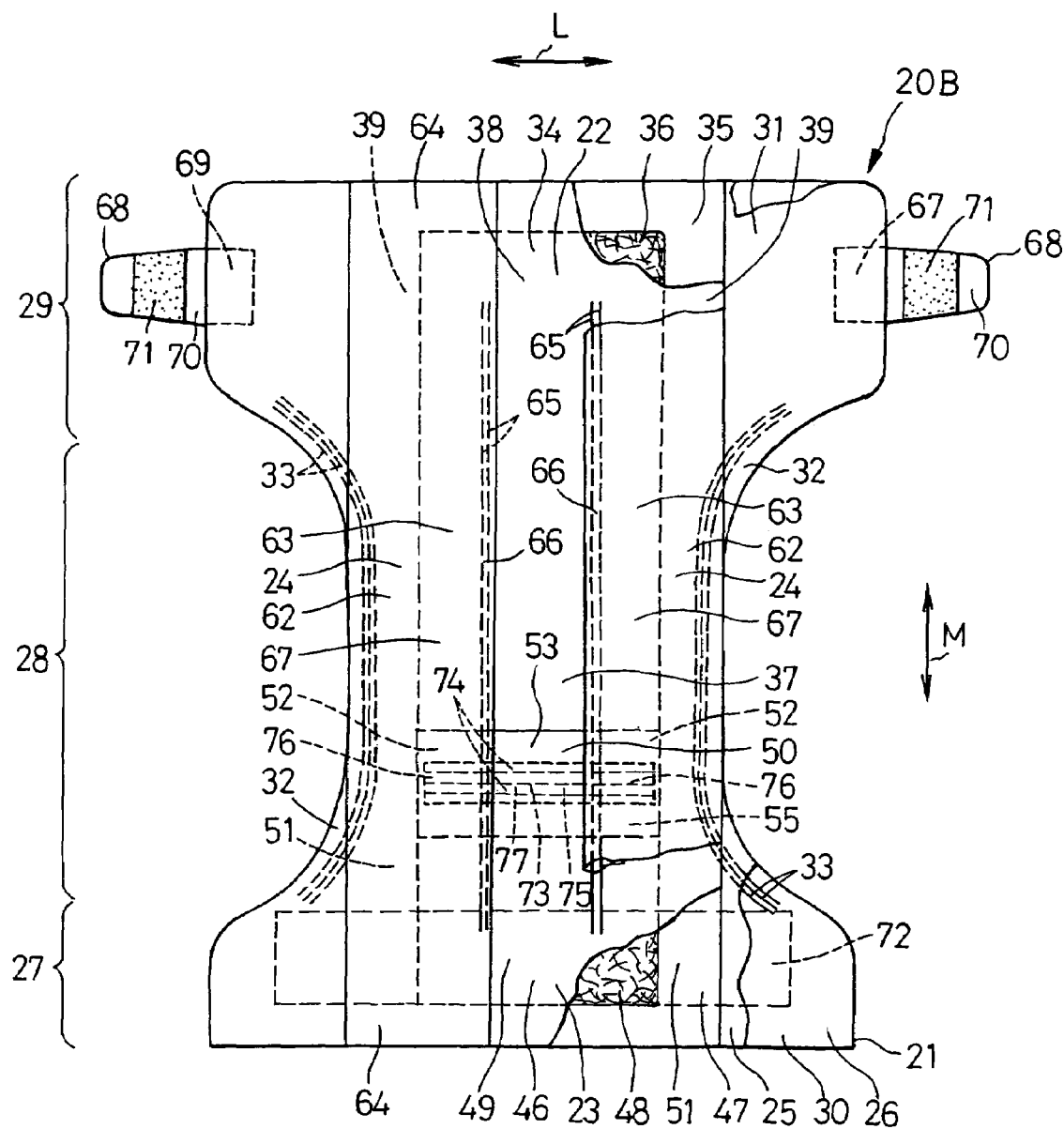
FIG. 6 is a partially cutaway plan view showing the diaper of FIG. 5 as viewed from the side of the panel.
Figure 7:
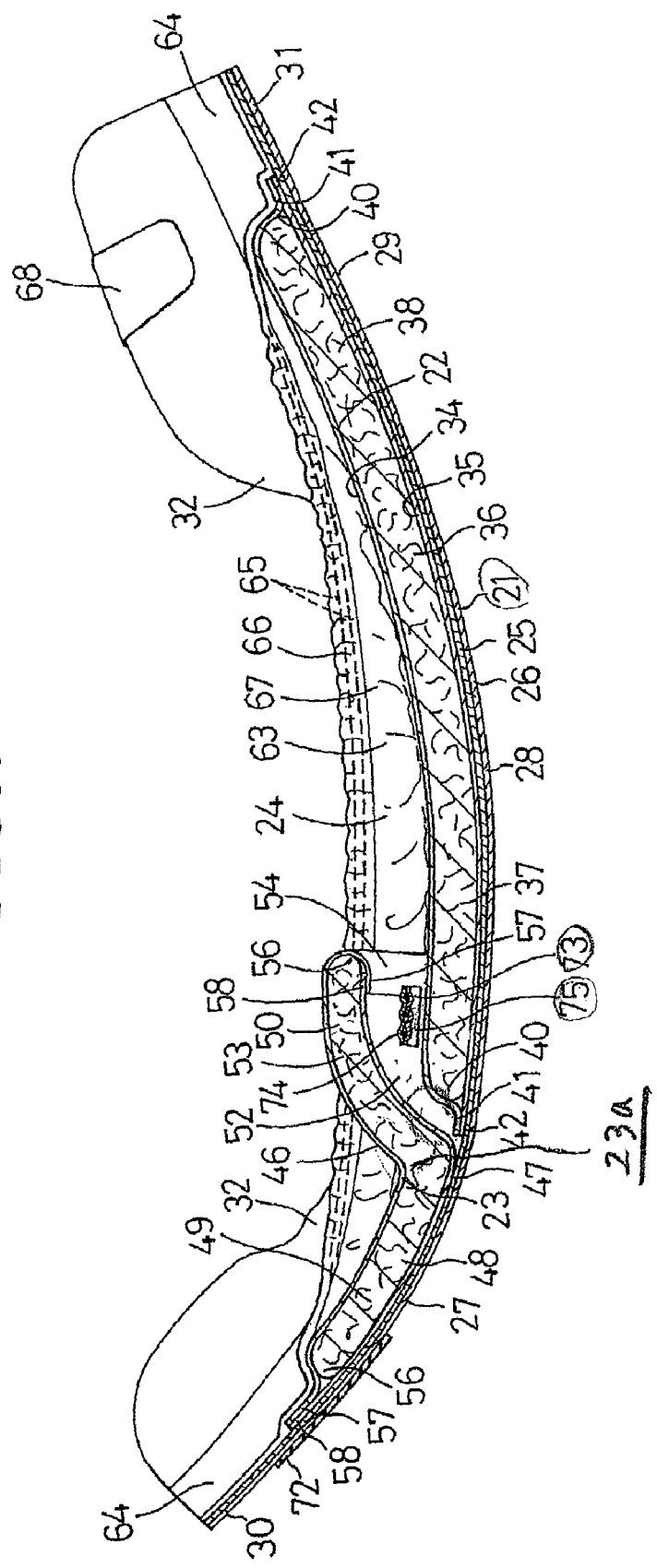
FIG. 7 is a sectional view taken along the line 7-7 in FIG. 5.
Figure 8:
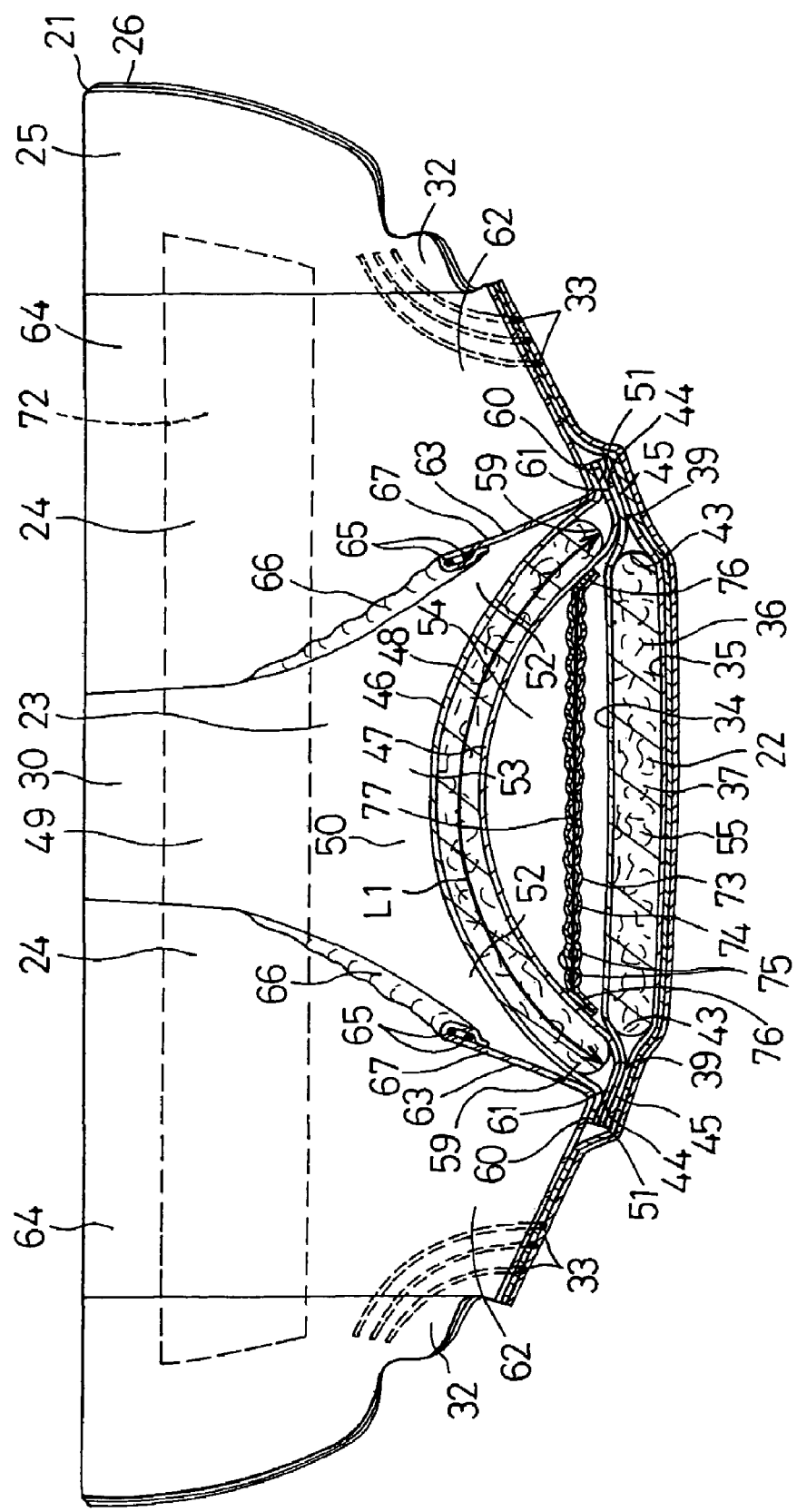
FIG. 8 is a sectional view taken along the line 8-8 in FIG. 5.

FIG. 5 is a perspective view showing a disposable diaper 20B according to another embodiment of the invention, FIG. 6 is a partially cutaway plan view showing the diaper 20B of FIG. 5 as viewed from the side of first and second panels 22, 23, FIG. 7 is a sectional view taken along the line 7-7 in FIG. 5 and FIG. 8 is a sectional view taken along the line 8-8 in FIG. 5. In FIGS. 5 and 6, a transverse direction is indicated by an arrow L, a longitudinal direction is indicated by an arrow M and a thickness direction is indicated by an arrow N (in FIG. 5 alone). FIG. 6 shows the diaper 20B as developed against contractile force of elastic members 33, 65, 74 in the longitudinal direction as well as in the transverse direction.

This diaper 20B is similar to the diaper 20A of FIGS. 1-4 except an arrangement such that the pocket 54 is provided with a spacer 73 extending in the transverse direction. The components similar to those in the diaper 20A of FIGS. 1-4 are designated by the same reference numerals as those in FIGS. 1-4 and the similar arrangements as those of the diaper 20A of FIGS. 1-4 will not be repetitively described here.

The spacer 73 is elastically stretchable in the transverse direction and contractibly attached to the pocket 54. Specifically, the spacer 73 comprises a water-pervious sheet 75 to which a plurality of stretchable elastic members 74 extending in the transverse direction are contractibly attached. These elastic members 74 are secured to the sheet 75 while the elastic members 74 are stretched at a predetermined ratio in the transverse direction. The spacer 73 has transversely opposite fixed ends 76 joined to the transversely opposite lateral sections 52 of the distal portion 50 of the second panel 23 and an intermediate section 77 extending between these ends 76. The transversely opposite lateral sections 52 of the distal portion 50 of the second panel 23 are drawn inward as viewed in the transverse direction of the chassis 21 under contractile force of the spacer 73.

Alternatively, the ends 76 of the spacer 73 may be interposed between the chassis 21 and the respective leak-barrier sheets 24 and joined to the lateral sections 32 of the sheet 31 and the side edges 62 of the sheets 24 instead of being joined to the lateral sections 52 of the distal portion 50. It is also possible to interpose the ends 76 of the spacer 73 between the chassis 21 and the respective leak-barrier sheets 24 and to join these ends 76 to the lateral sections 32 of the chassis 21 and to the side edges 62 of the respective leak-barrier sheets 24 as well as to the lateral sections 52 of the distal portion 50.

Without departing from the scope of the invention, it is possible to adopt the spacer 73 made of an elastically stretchable water-pervious sheet having none of the elastic members, for example, an elastically stretchable hydrophilic fibrous nonwoven fabric. It is also possible to adopt the spacer 73 made of a non-stretchable water-pervious sheet alone, for example, a non-stretchable hydrophilic fibrous nonwoven fabric. When it is desired to adopt the spacer 73 made of such a non-stretchable water-pervious sheet, the spacer 73 is exploited to have a transverse dimension larger than a transverse dimension of the core 48 so that the transversely opposite lateral sections 52 of the distal portion 50 may be drawn inward as viewed in the transverse direction of the chassis 21.

Drawn inward as viewed in the transverse direction of the chassis 21 under contractile force of the spacer 73, the transversely opposite lateral sections 52 of the distal portion 50 rise above the chassis 21 and respectively describe upward convex circular arcs. As a result, the intermediate section 53 of the distal portion 50 of the second panel 23 describes an upward circular arc above the lateral sections 52.

In the diaper 20B, a contractile force of the spacer 73 normally biases the transversely opposite lateral sections 52 of the distal portion 50 of the second panel 23 to be drawn inward as viewed in the transverse direction of the chassis 21 and thereby keeps the distal portion 50 in an upward convex shape. In other words, there is no anxiety that the transversely opposite lateral sections 52 rising above the chassis 21 might be unintentionally collapsed. In this way, the shape of the pocket 54 formed between the chassis 21 and the distal portion 50 of the second panel 23 can be reliably maintained under a contractile force of the spacer 73 The diaper 20B is particularly advantageous in that the pocket 54 is not readily collapsed and reliably receive feces. Even when the wearer's body pressure is exerted upon the diaper 20B in its thickness direction and the distal portion 50 of the second panel 23 is collapsed, just at the moment that the diaper 20B is relieved of the body pressure, a contractile force of the spacer 73 causes the distal portion 50 to rise above the chassis 21 to describe the upward convex circular arc and the pocket 54 is formed again between the chassis 21 and the distal portion 50.

The transverse dimension of the contracted spacer 73 is preferably in a range of 20 to 93%, more preferably in a range of 50 to 80% with respect to the transverse dimension L1 between the transversely opposite side edges 59 of the core 48 constituting the second panel 23.

The spacer 73 including the elastic member 74 has a tensile stress in the transverse direction in a range of 0.5 to 1.5 N at a 100 to 250% stretched state. If the tensile stress of the spacer 73 is less than 0.5 N, the transversely opposite lateral sections 52 of the distal portion 50 will be insufficiently drawn inward as viewed in the transverse direction of the chassis 21 under a contractile force of the spacer 73 and, even if a slight body pressure is exerted upon the diaper 20B, the distal portion 50 of the second panel 23 may be readily collapsed to close the opening of the pocket. If the tensile stress of the spacer exceeds 1.5 N, the crotch region 28 will be excessively contracted inward in the transverse direction, resulting in the formation of a plurality of irregular gathers in the chassis 21, the front portion 37 of the first panel 22 and the distal portion 50 of the second panel 23. These irregular gathers will make it difficult not only to maintain the desired shape of the pocket 54 and, in addition, deteriorate the desired body fluid absorbing function of the first and second panels 22, 23. Consequentially, adequate absorption of urine and feces will be impossible in the crotch region 28. The diaper 20B provided with the spacer 73 having the tensile stress in the range as specified above allows the pocket 54 formed between the chassis 21 and the distal portion 50 of the second panel 23 to be reliably kept in the desired shape without deteriorating the body fluid absorbent function of the first and second panels 22, 23 in the crotch region. The tensile stress of the spacer 73 was measured by the method as follows:

(1) The spacer 73 (inclusive of the elastic members 74) was separated from the diaper 20B and then the spacer 73 was cut to obtain samples for measurement of the stretch stress having a longitudinal dimension of 30 mm and a transverse dimension of 100 mm. For measurement of the stretch stress of the spacer 73, the Tensile Tester manufactured by SHIMADZU CORPORATION in Japan was used.

(2) Transversely opposite side edge portions of the sample contracted under a contractile force of the elastic members were clamped by respective chucks of the Tensile Tester (a dimension over which each end portion was clamped by the chuck: about 30 mm, a length dimension of the sample measured between the chucks: about 100 mm). The sample was stretched in the transverse direction at a rate of 100 mm/min and, after the sample had been stretched by 260%, the tension was relieved. The sample was stretched again in the transverse direction at a rate of 100 mm/min and a force exerted on the Tester at the moment the sample was stretched by 100 to 250% was measured as the tensile stress of the spacer in the transverse direction. The tensile stress in the transverse direction of the sample having been measured in this manner was in a range of 0.5 to 1.5 N. As used herein "the sample was stretched by 200%" means that, for example, the sample having its transverse dimension of 30 mm was stretched to 30 mm×2.0=60 mm.

Figure 9:
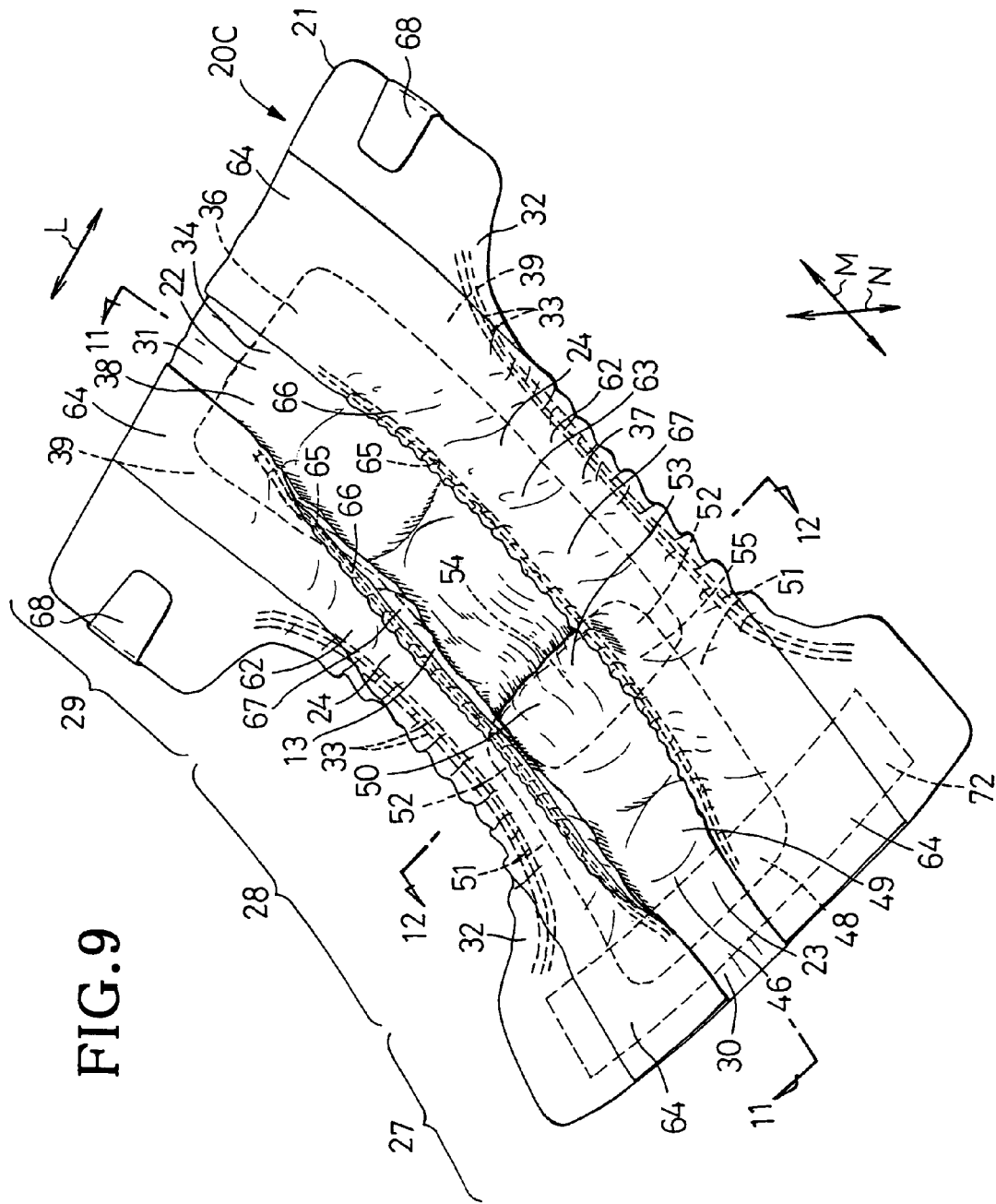
FIG. 9 is a perspective view showing a disposable diaper according to still another embodiment of the invention.
Figure 10:
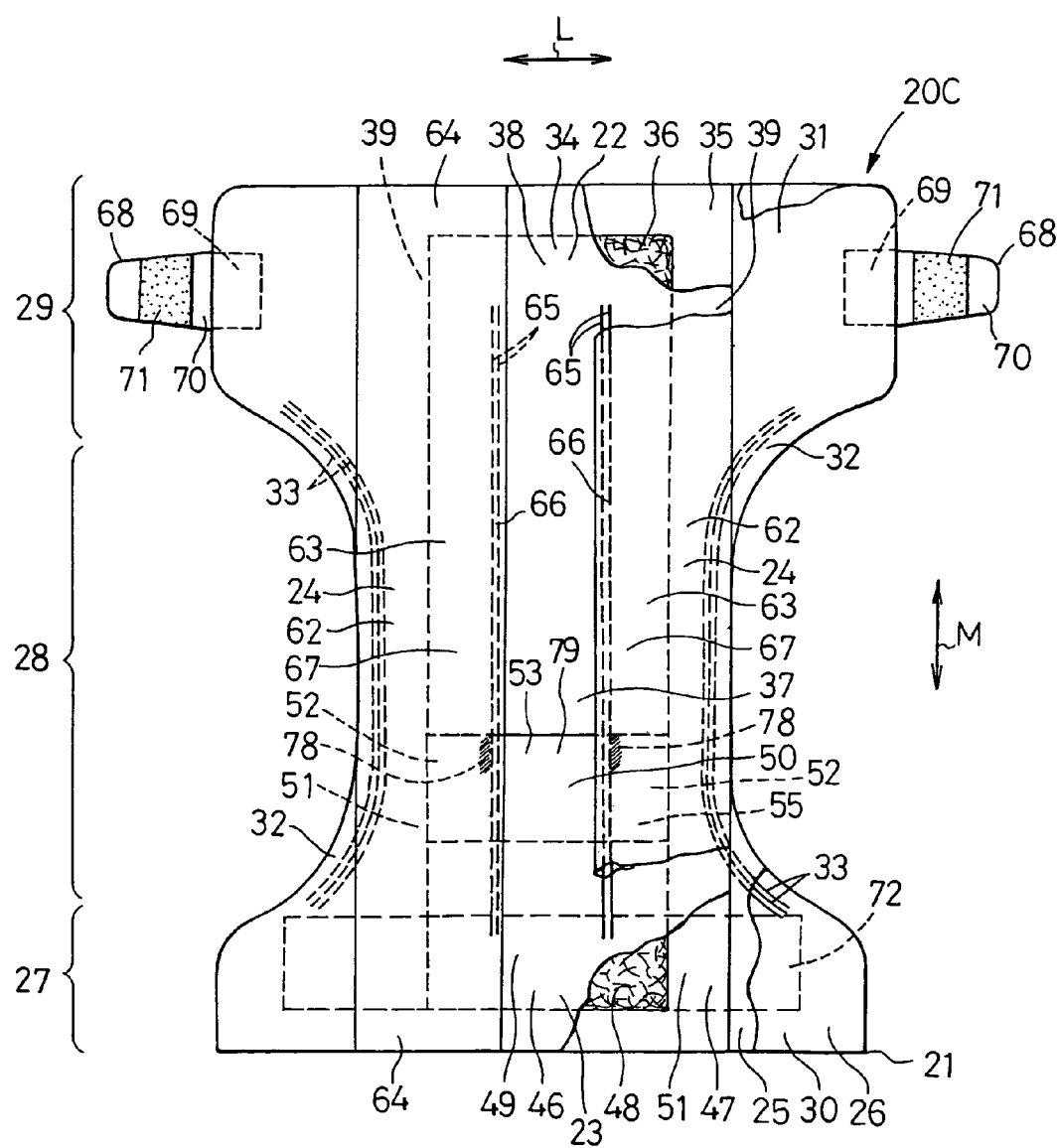
FIG. 10 is a partially cutaway plan view showing the diaper of FIG. 9 as viewed from the side of the panel.
Figure 11:
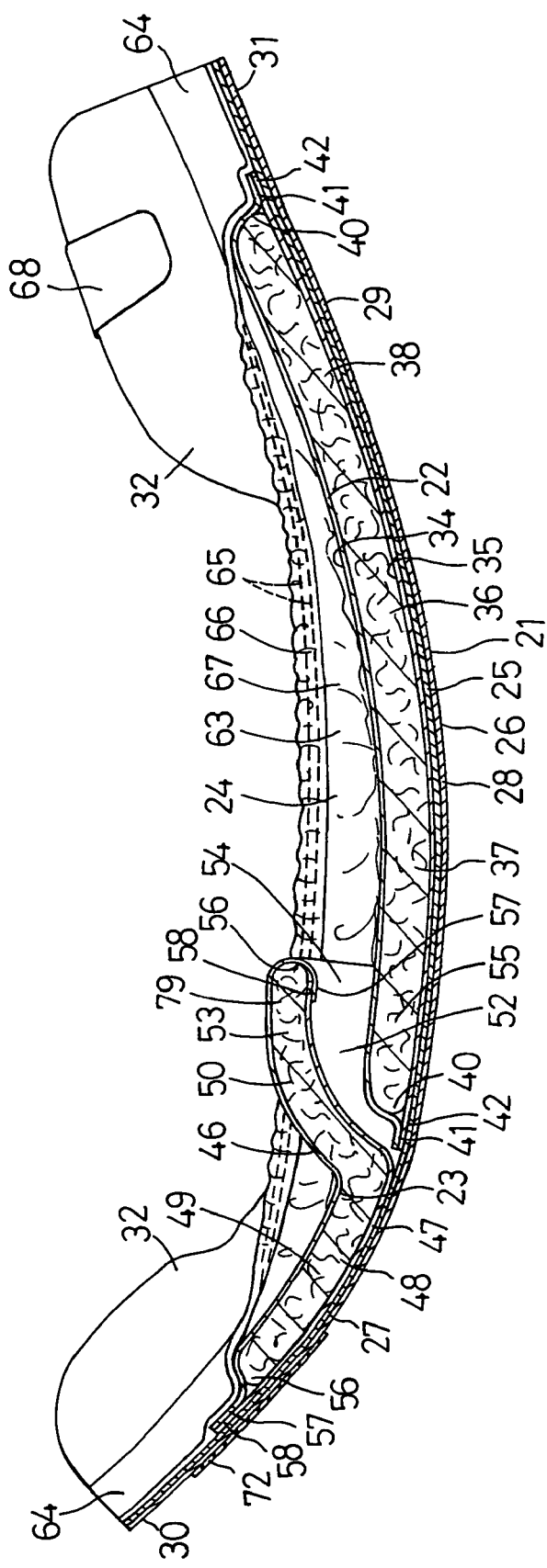
FIG. 11 is a sectional view taken along the line 11-11 in FIG. 9.
Figure 12:
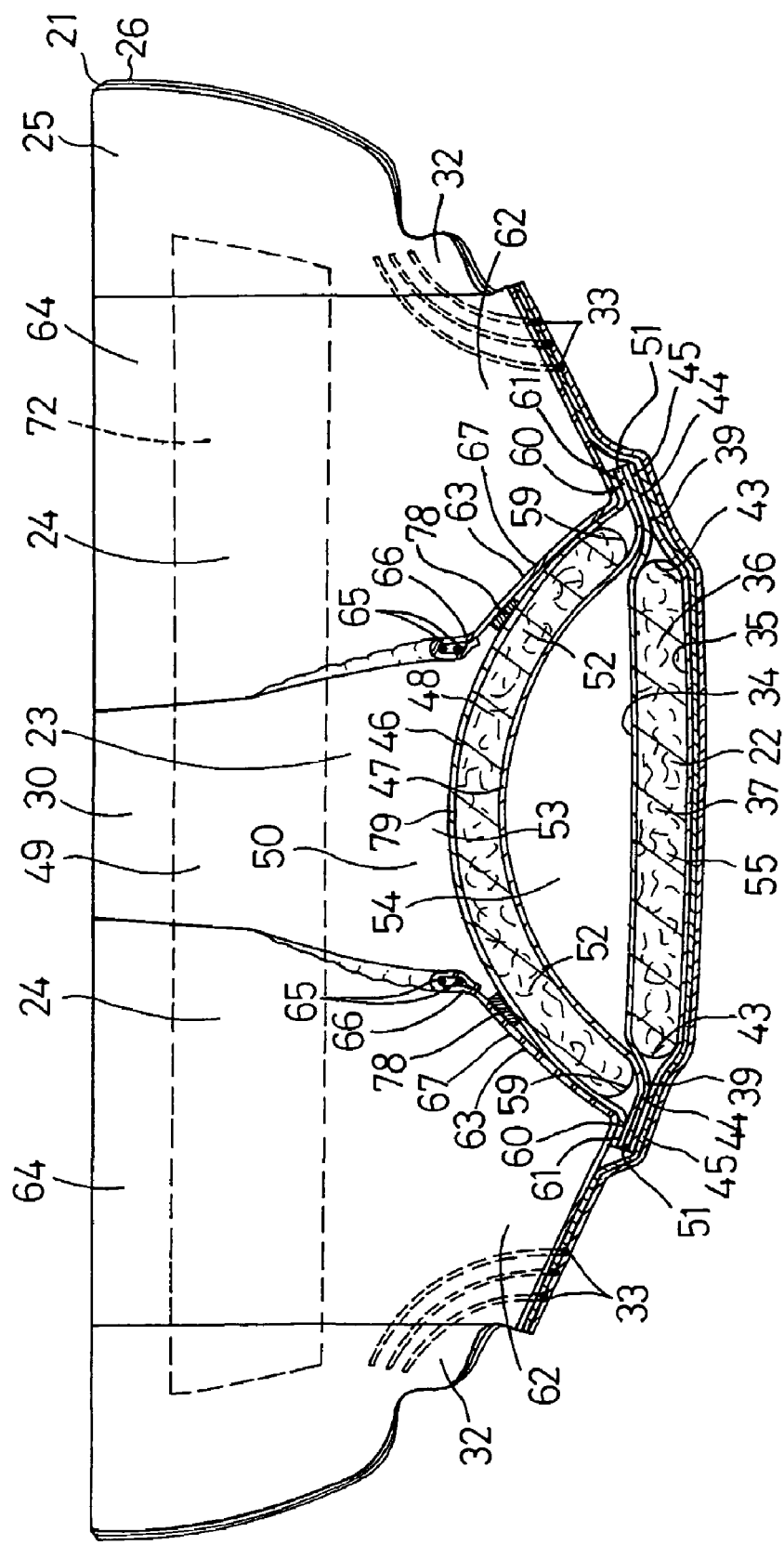
FIG. 12 is a sectional view taken along the line 12-12 in FIG. 9.

FIG. 9 is a perspective view showing a disposable diaper 20C according to still another embodiment of the invention, FIG. 10 is a partially cutaway plan view showing the diaper 20C of FIG. 9 as viewed from the side of first and second panel 22, 23, FIG. 11 is a sectional view taken along the line 11-11 in FIG. 9 and FIG. 12 is a sectional view taken along a line 12-12 in FIG. 9. In FIGS. 9 and 10, a transverse direction is indicated by an arrow L, a longitudinal direction is indicated by an arrow M and a thickness direction is indicated by an arrow N (in FIG. 9 alone). FIG. 10 shows the diaper 20C as developed against contractile force of elastic members 33, 65 in the longitudinal direction as well as in the transverse direction.

The diaper 20C further includes a pair of liquid-impervious leak-barrier sheets 24 laid on the inner side of the chassis 21 and extending in the longitudinal direction. This diaper 20C is similar to the diaper 20A of FIG. 1 except an arrangement such that the transversely opposite lateral sections 52 of the distal portion 50 of the second panel 23 are connected to the distal sections 63 of the respective leak-barrier sheets 24. The components similar to those in the diaper 20A of FIGS. 1-4 are designated by the same reference numerals as those in the diaper 20A of FIGS. 1-4 and the similar arrangements as those shown in FIGS. 1-4 will not be repetitively described here.

The distal portion 50 of the second panel 23 has the transversely opposite lateral sections 52 partially connected with the middle sections 67 of the distal sections 63 of the respective leak-barrier sheets 24 positioned aside toward the distal edges 66. Along the lateral sections 52, the liquid-pervious sheet 46 has its outer surface joined to the respective leak-barrier sheets 24 by means of adhesives 78. The distal edges 66 extend upward above the lateral sections 52. The intermediate section 53 of the distal portion 50 has an apex 79 lying above the distal edges 66. The distal sections 63 of the respective leak-barrier sheets 24 rise above the chassis 21 to form the barriers against bodily wastes and thereby bias the lateral sections 52 of the distal sections 63 to rise above the chassis 21. Alternatively, the lateral sections 52 of the distal portion 50 may be entirely connected with the middle sections 67 of the distal sections 63 or the distal sections 63 of the respective leak-barrier sheets 24 including the distal edges 66 may be entirely connected with the lateral sections 52 of the distal portion 50.

The lateral sections 52 raised by the distal sections 63 of the respectively leak-barrier sheets 24 extend upward above the chassis 21 so as to describe upward convex circular arcs. The intermediate section 53 correspondingly rises above the lateral sections 52 so as to describe an upward convex circular arc. Between the chassis 21 and the distal portion 50 of the second panel 23, a pocket 54 opening from the crotch region 28 toward the rear waist region 29 is formed. The pocket 54 extends over a generally front half of the crotch region 28 starting from a generally middle zone of the crotch region 28, as viewed in the longitudinal direction. The front portion 37 of the first panel 22 has a distal section 55 underlying the distal potion 50 of the second panel 23 and extending into the pocket 54.

The distal portion 50 of the second panel 23 have the respective lateral sections 52 raised above the chassis 21 as the distal sections 63 of the respective leak-barrier sheets 24 rise above the chassis 21. The shape of the distal portion 50 is reliably kept by the distal sections 63 of the respective leak-barrier sheets 24 to be convex upward above the chassis 21 since it is unlikely that the lateral sections 52 extending upward above the chassis 21 might be unintentionally collapsed. In this way, the distal sections 63 of the respective leak-barrier sheets 24 can be effectively utilized to reliably keep the shape of the pocket 54 formed between the chassis 21 and the distal portions 50 of the second panel 23. The diaper 20C is particularly advantageous in that the pocket 54 is hard to be closed and can reliably receive feces.

In the case of the diaper 20C also, the barriers formed by the distal sections 63 of the respective leak-barrier sheets 24 against urine are effective to prevent urine from leaking sideways beyond the side edge portions of the chassis 21 even if urine spreadings on the respective upper surface (i.e., the upper surface of the liquid-pervious sheets 34) of the first panel 22 flows toward the side edges 39.

The distal edges 66 of the distal sections of the respective leak-barrier sheets 24 extend upward above the lateral sections 52 of the distal portion 50 and thereby form the barriers against bodily wastes. Even if urine spreadings over the upper surface (i.e., upper surface of the liquid-pervious sheet 46) of the distal portion 50 of the second panel 23 moves toward the lateral sections 52 of the distal portion 50, the above-mentioned arrangement allows it to prevent urine from further moving toward the lateral sections 52 and thereby to prevent urine leaking sideways beyond the lateral sections 52 of the distal portion 50. The apex 79 of the intermediate section 53 of the distal portion 50 lies above the distal edges 66 and therefore the apex 79 of the intermediate comes in contact with the wearer's crotch region ahead of the distal edges 66. Consequentially, it is unlikely that the distal edges 66 might be collapsed in the transverse direction of the diaper 20C and the function of these distal edges 66 as the barriers against urine might be disabled.

Figure 13:
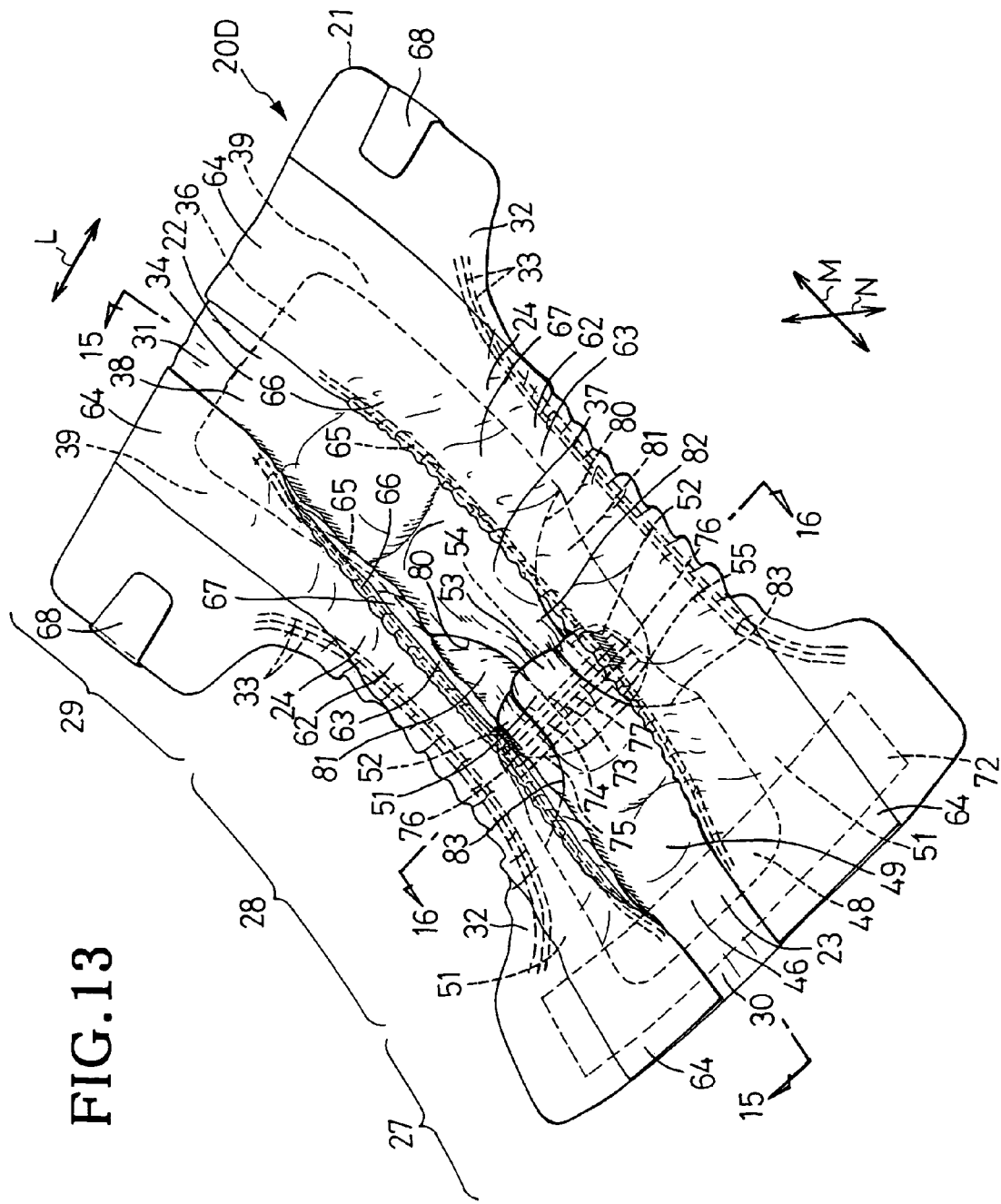
FIG. 13 is a perspective view showing a disposable diaper according to further another embodiment of the invention.
Figure 14:
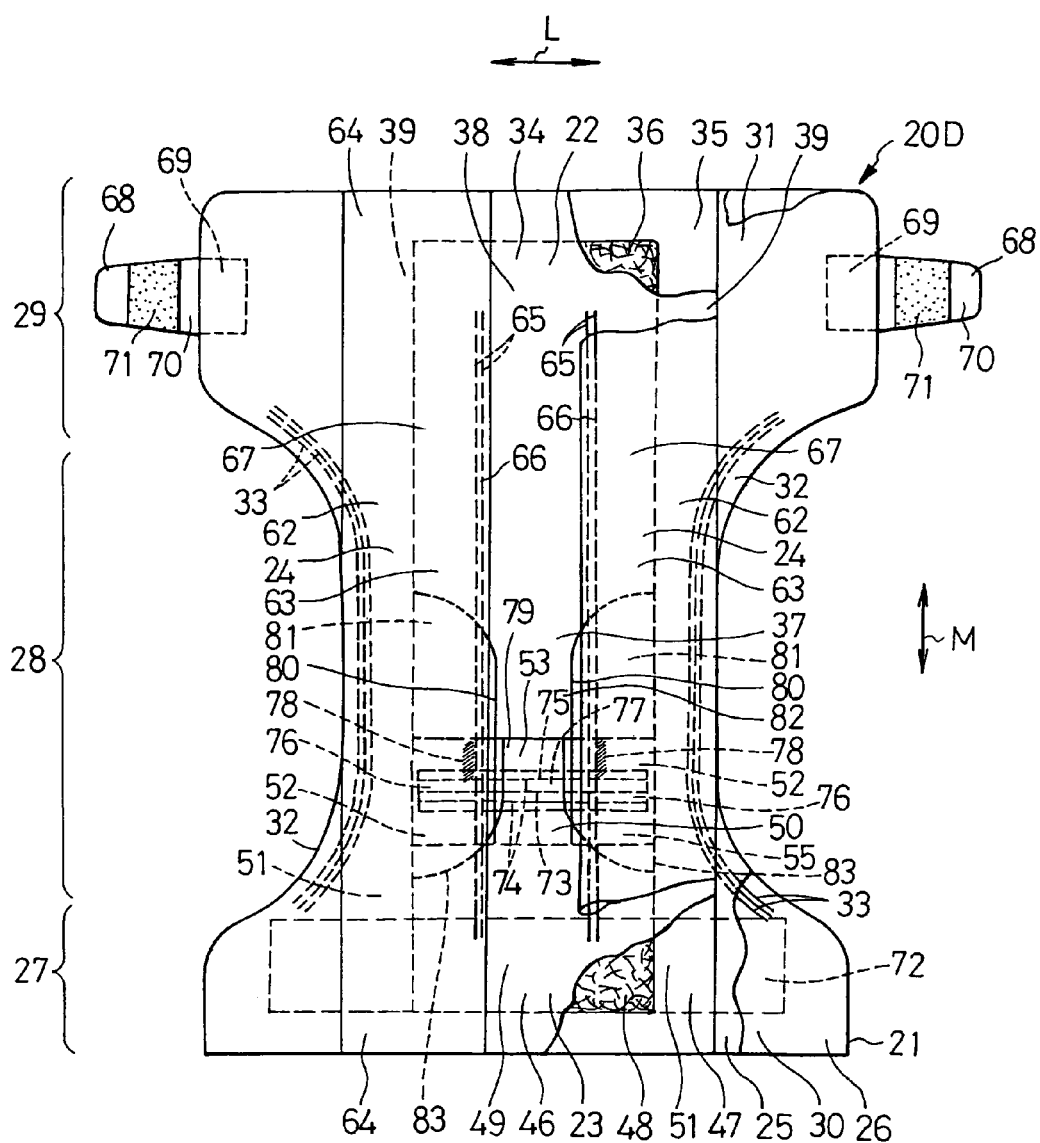
FIG. 14 is a partially cutaway plan view showing the diaper of FIG. 13 as viewed from the side of the panel.
Figure 15:
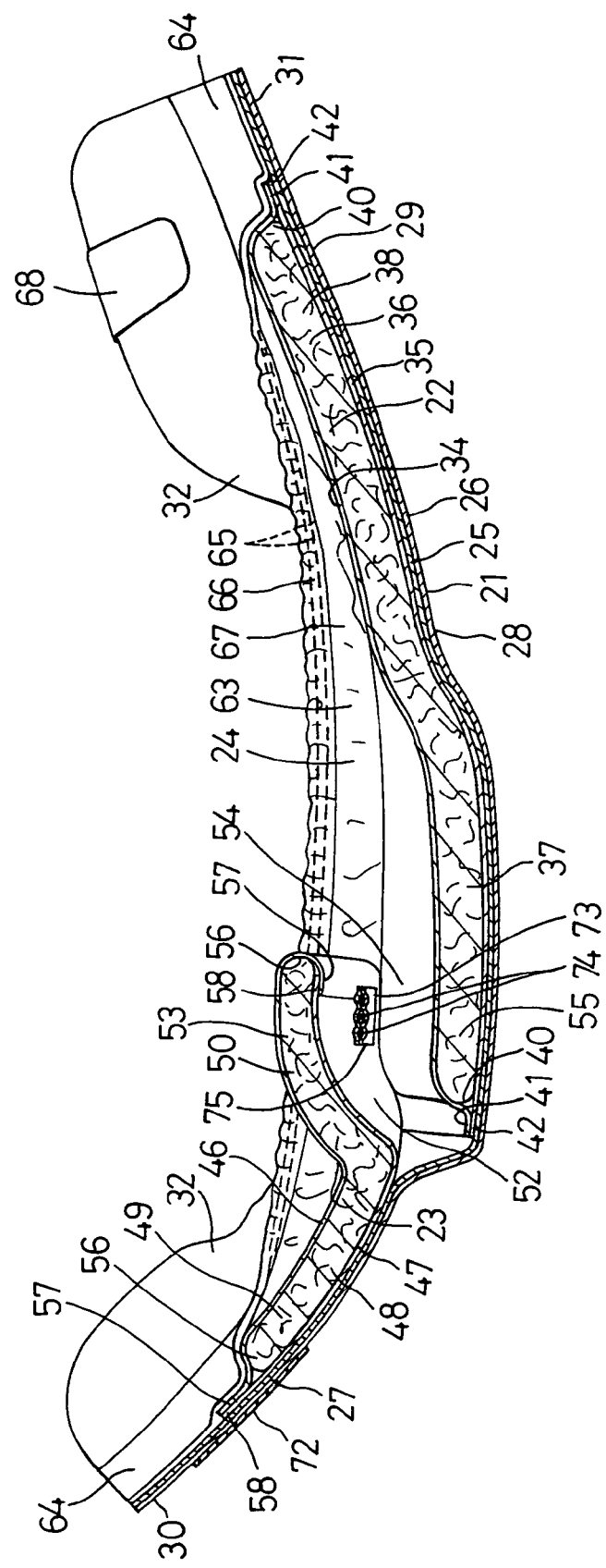
FIG. 15 is a sectional view taken along the line 15-15 in FIG. 13.
Figure 16:
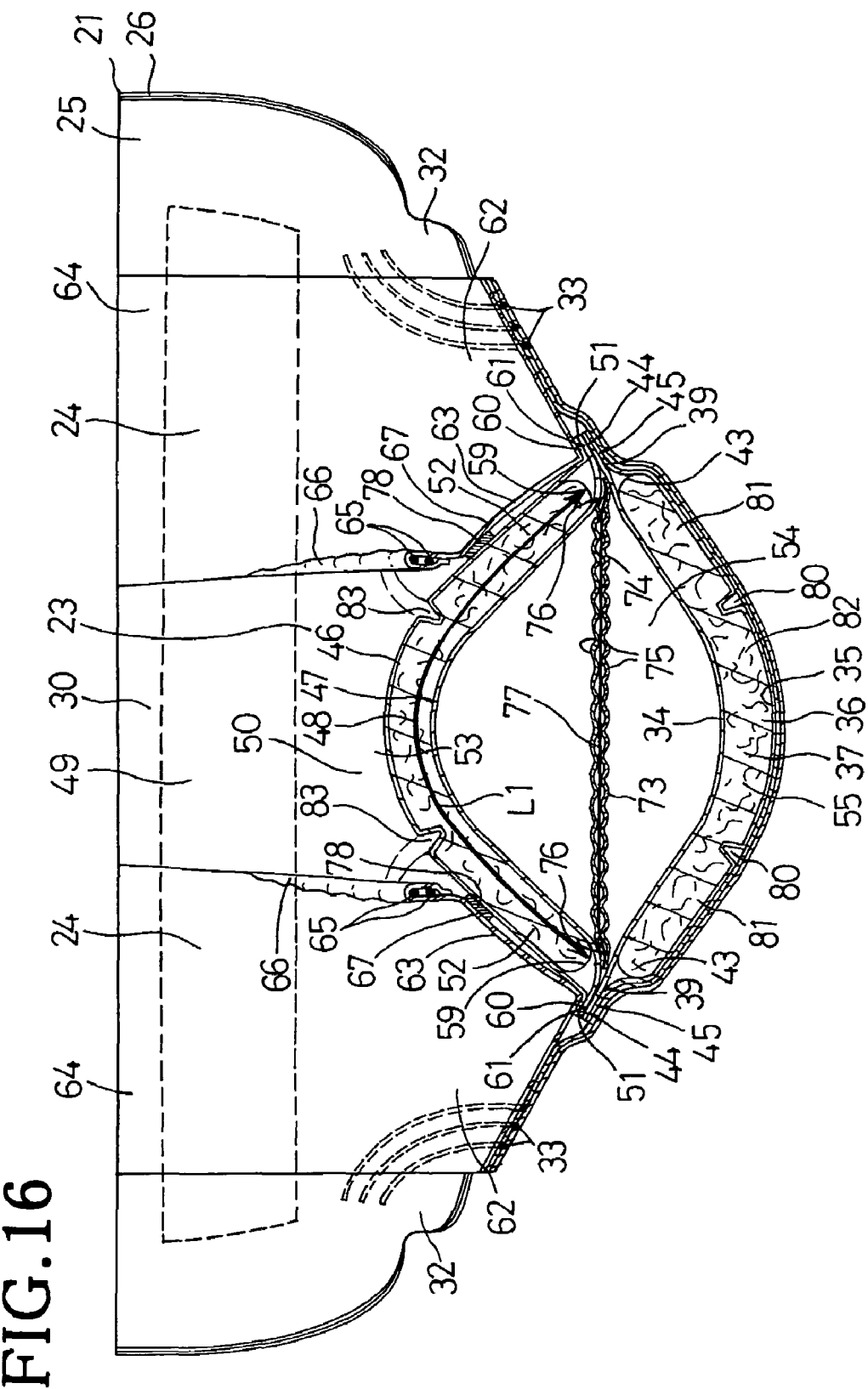
FIG. 16 is a sectional view taken along the line 16-16 in FIG. 13.

FIG. 13 is a perspective view showing a disposable diaper 20D according to further another embodiment of the invention, FIG. 14 is a partially cutaway plan view showing the diaper 20D of FIG. 13 as viewed from the side of first and second panels 22, 23, FIG. 15 is a sectional view taken along the line 15-15 in FIG. 13 and FIG. 16 is a sectional view taken along the line 16-16 in FIG. 13. In FIGS. 13 and 14, a transverse direction is indicated by an arrow L, a longitudinal direction is indicated by an arrow M and a thickness direction is indicated by an arrow N (in FIG. 13 alone). FIG. 14 shows the diaper 20C as developed against contractile force of elastic members 33, 65 in the longitudinal direction as well as in the transverse direction.

This diaper 20D is similar to the diaper 20A of FIGS. 1-4 except an arrangement such that the first and second panels 22, 23 are formed with folding guides 80, 83, the pocket 54 is provided with the spacer 73 and the lateral sections 52 of the distal portion 50 of the second panel 23 are connected with the distal sections of the respective leak-barrier sheets 24. The components similar to those in the diaper 20A of FIGS. 1-4 are designated by the same reference numerals as those in the diaper 20A of FIGS. 1-4 and the similar arrangements as those shown in FIGS. 1-4 will not be repetitively described here.

The front portion 37 of the first panel 22 is formed with a pair of folding guides 80 extending in a generally longitudinal direction and spaced apart from each other by a predetermined dimension in the transverse direction. Specifically, these folding guides 80 extend from the front portion 37 to the side edges 39, describing circular arcs which are convex inward as viewed in the transverse direction of the chassis 21. The front portion 37 is divided into transversely opposite lateral sections 81 defined outside the respective folding guides 80 and an intermediate section 82 defined between the respective folding guides 80. The front portion 37 is folded inward along the folding guides 80. The lateral sections 81 and the intermediate section 82 of the front portion 37 describe together with the chassis 21 circular arcs which are convex downward in the thickness direction of the diaper 20D.

A pair of folding guides 83 are also formed between the opposite lateral sections 52 and the middle section 53 in the distal portion 50 of the second panel 23 wherein these folding guides 83 are spaced apart from each other in the transverse direction by a predetermined dimension and extend in a generally longitudinal direction. Specifically, these folding guides 83 extend from the distal portion 50 to the opposite side edges 51, describing circular arcs which are convex inward as viewed in the transverse direction of the chassis 21. The distal portion 50 is folded inward along the folding guides 83.

The cores 36, 48 respectively constituting the first and second panels 22, 23 along these folding guides 80, 83 have a density, basis weight and thickness dimension less than those of the cores 36, 48 respectively constituting the fixed front portion 37 of the first panel 22 and the distal portion 50 of the second panel 23 except for the folding guides 80, 83. Correspondingly, the first and second panels 22, 23 along these folding guides 80, 83 present a stiffness lower than that presented by the front portion 37 (containing the core 36) of the first panel 22 as well as the distal portion 50 (containing the core 48) of the second panel 23 both except for the folding guides 80, 83. A density, basis weight and thickness dimension, at least a density and basis weight of the cores 36, 48 respectively constituting the first and second panels 22, 23 along these folding guides 80, 83 may be adjusted to be less than those of the cores 36, 48 respectively constituting the front portion 37 of the first panel 22 and the distal portion 50 of the second panel 23 except for the folding guides 80, 83 to establish the desired relationship that the first and second panels 22, 23 along these folding guides 80, 83 has a stiffness lower than that presented by the front portion 37 (containing the core 36) of the first panel 22 as well as the distal portion 50 (containing the core 48) of the second panel 23 both except for the folding guides 80, 83.

Alternatively, these folding guides 80, 83 may contain neither the core 36 nor the core 48, i.e., the folding guides 80 may be formed from the liquid-pervious sheet 34 and the liquid-impervious sheet 35 except for the core 36 while the folding guides 83 may be formed from the liquid-pervious sheets 46, 47 except for the core 48. An arrangement is also possible without departing from the scope of the invention such that, in the first and second panels 22, 23, the folding guides 80 extend from the front portion 37 in the longitudinal direction and terminate short of the transversely opposite side edges 39 while the folding guides 83 extend from the distal portion 50 in the longitudinal direction and terminate short of the transversely opposite side edges 51.

The spacer 73 is elastically stretchable in the transverse direction and contractibly attached to the pocket 54. Specifically, the spacer 73 comprises a water-pervious sheet 75 to which a plurality of stretchable elastic members 74 extending in the transverse direction and spaced one from another in the longitudinal direction are contractibly attached. These elastic members 74 are secured to the sheet 75 while the elastic members 74 are stretched at a predetermined ratio in the transverse direction. The spacer 73 has transversely opposite ends 76 joined to the transversely opposite lateral sections 52 of the distal portion 50 of the second panel 23 and an intermediate section 77 extending between these ends 76. The transversely opposite lateral sections 52 of the distal portion 50 of the second panel 23 are drawn inward as viewed in the transverse direction of the chassis 21 under a contractile force of the spacer 73.

The distal portion 50 of the second panel 23 has the transversely opposite lateral sections 52 connected with the middle sections 67 of the distal sections 63 of the respective leak-barrier sheets 24 put aside toward the respective distal edges 66. Along the lateral sections 52, the outer surface of the liquid-pervious sheet 46 is joined to the respective leak-barrier sheets 24 by means of adhesives 78. The distal edges 66 extend upward above the lateral sections 52 of the distal portion 50. The apex 79 of the intermediate section 53 of the distal portion 50 lies at a level above the distal edges. The distal sections 63 rise above the chassis 21 to form the barriers against bodily wastes and thereby bias the lateral sections 52 of the distal portion 50 to rise above the chassis 21.

The transversely opposite lateral sections 52 of the distal portion 50 are folded inward along the folding guides 83, drawn inward by the spacer 73 as viewed in the transverse direction of the chassis 21 and raised above the chassis 21 by the distal sections 63 of the respective leak-barrier sheets 24. Of the distal portion 50, the transversely opposite lateral sections 52 extend upward above the chassis 21 and the intermediate section 53 describes the circular arc which is convex upward above the lateral sections 52. A pocket 54 opening from the crotch region 28 toward the rear waist region 29 is formed between the chassis 21 and the distal portion 50 of the second panel 23. Below the distal portion 50 of the second panel 23, a distal section 55 of the front portion 37 of the first panel 22 extends into the pocket 54. The distal section 55 cooperates with the chassis 21 to form the pocket 54 which is convex downward in the thickness direction of the diaper 20D.

The front portion 37 of the first panel 22 is depressed together with the chassis 21 to be convex downward in the thickness direction of the diaper 20D while the distal portion 50 of the second panel 23 becomes convex upward above the chassis 21 so that the pocket 54 opening from the crotch region 28 toward the rear waist region 29 may be formed between the chassis 21 and the distal portion 50. Such an arrangement allows feces discharged onto the rear half of the crotch region 28 and the rear waist region 29 to be received by the pocket 54 even if feces moves toward the front waist region 27. The fixed front portion 37 of the first panel 22 is depressed together with the chassis 21 to be convex downward in the thickness direction of the diaper 20D. Such an arrangement allows the pocket 54 to assure a capacity for reception of feces higher than those assured by the diapers 20A, 20B, 20C shown in FIGS. 1, 5 and 9, respectively. In this way, a larger amount of feces discharged onto the diaper 20D can be reliably received by the pocket 54.

The folding guides 83 extend from the distal portion 50 to the opposite side edges 51 of the second panel 23 and the distal portion 50 is folded along the folding guides 83 so that the distal portion 50 of the second panel 23 may be distinctly divided into the transversely opposite lateral sections 52 defined outside the respective folding guides 83 and the intermediate section 53 defined between the pair of folding guides 83 and the lateral sections 52 defined outside the respective folding guides 83 may be facilitated to rise above the chassis 21. The opposite lateral sections 52 defined outside the respective folding guides 83 are thereby facilitated to rise above the chassis 21 and the distal portion 50 of the second panel 23 is facilitate to be convex upward above the chassis 21. In this manner, the pocket 54 can be reliably formed between the chassis 21 and the distal portion 50 of the second panel 23.

The pocket 54 is provided with a spacer 73 which is elastically stretchable in the transverse direction and contractibly attached thereto. The transversely opposite lateral sections 52 of the distal portion 50 of the second panel 23 are drawn inward as viewed in the transverse direction of the chassis 21 under a contractile force of the spacer 73 and the distal portion 50 is kept in an upward convex shape. In other words, there is no anxiety that the transversely opposite lateral sections 52 rising above the chassis 21 might be unintentionally collapsed. In this way, the shape of the pocket 54 formed between the chassis 21 and the distal portion 50 of the second panel 23 can be reliably maintained under a contractile force of the spacer 73. Even when the wearer's body pressure is exerted upon the diaper 20D in its thickness direction and the distal portion 50 of the second panel 23 is collapsed, just at the moment that the diaper 20D is relieved of the body pressure, a contractile force of the spacer 73 causes the distal portion 50 to rise above the chassis 21 to describe the upward convex circular arc and the pocket 54 is formed again between the chassis 21 and the distal portion 50.

The distal sections 63 of the respective leak-barrier sheets 24 rising above the chassis 21 bias the distal portion 50 of the second panel 23 to rise above the chassis 21 so that the distal portion 50 may be kept by the distal sections 63 of the respective leak-barrier sheet 24 in an upward convex shape and the lateral sections 52 of the distal portion 50 extending upward above the chassis 21 may be protected from being unintentionally collapsed. Consequentially, the distal sections 63 of the respective leak-barrier sheets 24 can be effectively utilized to keep the pocket 54 formed between the chassis 21 and the distal portion 50 in a desired shape.

In the case of the diaper 20D also, the barriers formed by the distal sections 63 of the respective leak-barrier sheets 24 against urine are effective to prevent urine from leaking sideways beyond the side edge portions of the chassis 21 even if urine spreadings on the respective upper surface (i.e., the upper surface of the liquid-pervious sheets 34) of the first panel 22 flows toward the side edges 39.

In the case of the diaper 20D also, the distal edges of the distal sections 63 of the respective leak-barrier sheets 24 extend above the lateral sections 52 of the distal portion 50 and form the barriers against urine. The distal edges 66 effective to prevent urine from leaking sideways beyond the lateral sections 52 of the distal portion 50 even if urine spreadings on the upper surface (i.e., the upper surface of the liquid-pervious sheet 46) of the distal portion 50 flows toward the lateral sections 52. The apex 79 of the intermediate section 53 of the distal portion 50 lies at a level above the distal edges 66. Such a unique arrangement ensures that the apex 79 of the intermediate comes in contact with the wearer's crotch region ahead of the distal edges 66. Consequentially, it is unlikely that the distal edges 66 might be collapsed in the transverse direction of the diaper 20D and the function of these distal edges 66 as the barriers against urine might be disabled.

The spacer 73 functioning to draw the lateral sections 52 of the distal portion 50 inward as viewed in the transverse direction of the chassis 21 cooperates with the distal sections 63 of the respective leak-barrier sheets 24 functioning to raise the lateral sections 52 of the distal portion 50 to ensure that the pocket 54 is hardly closed and reliably receives feces.

The distal portion 50 (containing the core 48) of the second panel 23 including folding guides 83 has a transverse flexural stiffness in a range of 0.5 to 1.5 mN and the distal portion 50 (containing the core 48) of the second panel 23 except for the folding guides 83 has a transverse flexural stiffness in a range of 1.0 to 2.0 mN. If the stiffness of the distal portion 50 (containing the core 48) including the folding guides 83 exceeds 1.5 mN, it will be difficult to tuck the distal portion 50 along the folding guides 83 and to raise the lateral sections 52 above the chassis 21. If the stiffness of the distal portion 50 of the second panel 23 except for the folding guides 83 is less than 1.0 mN, the distal portion 50 will be excessively contracted inward as viewed in the transverse direction of the chassis 21 under a contractile force of the spacer 73. Consequentially, not only it will be impossible to keep the pocket 54 in its effective shape but also the body fluid absorbing function of the first and second panels 22, 23 in the crotch region 28 will be deteriorated and it will be difficult to achieve satisfactory absorption of urine in the crotch region 28. If the stiffness of the distal portion 50 of the second panel 23 except for the folding guides 83 exceeds 2.0 mN, a flexibility of the second panel will be deteriorated and the second panel 23 coming in contact with the diaper wearer's crotch region may uncomfortably irritate the diaper wearer. These stiffness values were measured using the Gurley Method (JIS L 1096-01-8.20.1) as follows:

(1) The second panel 23 was taken off from the diaper 20D and the second panel was cut to obtain samples each having a longitudinal dimension of 25 mm and a transverse dimension of 30 mm for measurement of stiffness values. As the samples for this measurement, the first sample including the folding guides 83 and the second sample (containing the core 48) except for the folding guides 83 were prepared. For measurement of the flexural stiffness, the Gurley's Stiffness Tester was used.

(2) One of longitudinally opposite ends of the first sample is held by a chuck of the tester and the other end portion is maintained in engagement with a pendulum of the tester and the tester is initialized by loading an auxiliary weight so that the tester scale may point the readings in a range of 3 to 6; the tester is turned on and a scale readings of the moment at which the pivot rod of the pendulum is separated from the first sample is recorded as a first stiffness value. Now the other of longitudinally opposite ends of the first sample is held by the chuck of the tester and the one of these ends is maintained in engagement with the pendulum of the tester. The tester is initialized by loading the auxiliary weight so that the tester scale may point the readings in a range of 3 to 6; the tester is turned on and a scale readings of the moment at which the pivot rod of the pendulum is separated from the sample is recorded as a second stiffness value. An average value of these first and second stiffness values obtained in this manner is recorded as the flexural stiffness value of the distal portion 50 of the second panel 23 including the folding guides 83. The flexural stiffness value of the first sample was in a range of 0.5 to 1.5 mN.

(3) One of longitudinally opposite ends of the second sample is held by a chuck of the tester and the other end portion is maintained in engagement with a pendulum of the tester and the tester is initialized by loading an auxiliary weight so that the tester scale may point the readings in a range of 3 to 6; the tester is turned on and a scale readings of the moment at which the pivot rod of the pendulum is separated from the second sample is recorded as a third stiffness value. Now the other of longitudinally opposite ends of the second sample is held by the chuck of the tester and the one of these ends is maintained in engagement with the pendulum of the tester. The tester is initialized by loading the auxiliary weight so that the tester scale may point the readings in a range of 3 to 6; the tester is turned on and a scale readings of the moment at which the pivot rod of the pendulum is separated from the sample is recorded as a fourth stiffness value. An average value of these third and fourth stiffness values obtained in this manner is recorded as the flexural stiffness value of the distal portion 50 (containing the core 48) of the second panel 23 except for the folding guides 83. The flexural stiffness value of the second sample was in a range of 1.0 to 2.0 mN.

This diaper 20D may alternatively arranged so that the first and second panels 22, 23 present a stiffness higher along the folding guides 80, 83 than in the fixed front portion 37 of the first panel 22 as well as the distal portion 50 of the second panel 23 both except for the folding guides 80, 83. As an example of measures to establish such relationship in this alternative arrangement, the first and second panels 22, 23 may be compressed in the thickness direction along the folding guides 80, 83 and thereby density and/or basis weight of the cores 36, 48 along the folding guides 80, 83 may be enhanced. In this case, the fixed front portion 37 is folded along the folding guides 80 and thereby divided into the opposite lateral sections 81 and the intermediate section 82 and the distal portion 50 is folded along the folding guides 83.

While the diapers 20A, 20B, 20C and 20D are illustrated with the front portion 49 of the second panel 23 being joined to the front waist region 27 of the chassis 21, it is also possible to join the front portion 49 to the front end 30 alone of the chassis 21. While the diapers 20C and 20D are respectively illustrated by FIGS. 9 and 13 to have the opposite side edges 51 of the second panel 23 joined over full length of these side edges 51 to the opposite lateral sections 32 of the chassis 21, it is also possible to join these side edges 51 only in the vicinity of the distal section of the second panel 23 to the opposite lateral sections 32 of the chassis 21. In other words, it not essential to join the side edges 51 over full length thereof to the lateral sections 32 of the chassis 21.

Assumed that each of these diapers 20A, 20B, 20C and 20D is divided by a transverse center line bisecting the longitudinal dimension thereof into front and rear halves and the front half is further divided by a transverse parting line into a middle section put aside toward the transverse center line and a distal section being remote from the transverse center line, the present invention can be effectively implemented so long as the distal portion 50 lies in this middle section of the diaper 20A, 20B, 20C or 20D.

Stock materials for the liquid-pervious sheets 34, 46, 47 may be selected from the group consisting of a hydrophilic fibrous nonwoven fabric, hydrophobic fibrous nonwoven fabric having a plurality of perforations and a plastic film having a plurality of fine apertures. Stock materials for the leak-barrier sheets 24 and the liquid-impervious sheet 35 may be selected from the group consisting of a hydrophobic fibrous nonwoven fabric, a breathable liquid-impervious plastic film, a composite nonwoven fabric comprising two or more hydrophobic fibrous nonwoven fabric layers laminated one upon another and a composite sheet comprising a hydrophobic fibrous nonwoven fabric and a breathable liquid-impervious plastic film laminated upon each other. It is possible without departing from the scope of the invention to form the chassis 21, the leak-barrier sheets 24 and the liquid-impervious sheet 35 using a composite nonwoven fabric (SM nonwoven fabric, SMS nonwoven fabric or SMMS nonwoven fabric) consisting of a melt blown fibrous nonwoven fabric having a high water-resistance and a spun bond fibrous nonwoven fabric being high in strength as well as in flexibility laminated on at least one side of the melt blown fibrous nonwoven fabric.

Stock materials for the fibrous nonwoven fabric layers may be selected from the group consisting of spun lace-, needle punch-, melt blown-, thermal bond-, spun bond- and chemical bond-nonwoven fabric layers. Component fibers of these nonwoven fabric layers may be selected from the group consisting of polyester-, polyacrylonitril-, polyvinyl chloride-, polyethylene-, polypropylene- and polystyrene-based fibers. It is also possible without departing from the scope of the invention to use the component fibers selected from the group consisting of core-sheath conjugate fibers, side-by-side conjugate fibers, modified macaroni fibers, microporous fibers and fused type conjugate fibers.

The stretchable hydrophilic fibrous nonwoven fabric forming the water-pervious sheet may be of a melt blown nonwoven fabric or a spun bond nonwoven fabric. As component fiber for the stretchable fibrous nonwoven fabric, stretchable fibers obtained by a melt spinning thermoplastic elastomer resin. It is possible without departing from the scope of the invention to form the water-pervious sheet using a composite nonwoven fabric comprising a hydrophilic stretchable fibrous nonwoven fabric made of thermoplastic elastomer resin fibers and a hydrophilic fibrous nonwoven fabric made of crimped fibers obtained by a melt spinning thermoplastic synthetic resin selected from the group consisting of polypropylene, polyethylene and polyester laminated on at least one surface of the hydrophilic stretchable fibrous nonwoven fabric.

Each of the cores 36, 48 comprises a mixture of particulate or fibrous super-absorbent polymers and fluff pulp fibers or a mixture of particulate or fibrous super-absorbent polymers, fluff pulp fibers and thermoplastic synthetic resin fibers, in any case, suitably compressed to a predetermined thickness dimension. Consequentially, the cores 36, 48 have a stiffness higher than that of the chassis 21 and sheets 24, 34, 35, 46, 47. The cores 36, 48 are entirely wrapped with liquid-pervious sheets (not shown) such as tissue papers or hydrophilic fibrous nonwoven fabrics in order to prevent the cores 36, 48 from getting out of respective initial shapes thereof.

Joining of the sheets 35, 47 to the chassis 21, joining of the sheets 34, 35, 46, 47 one to another, joining of the cores 36, 48 to the sheets 34, 35, 46, 47, and securing of the elastic members 33, 65 to the chassis 21 and the sheet 24 may be achieved by using adhesives or welding technique such as heat-sealing or sonic sealing. Adhesives may be selected from the group consisting of hot melt adhesive, acrylic adhesive, rubber-based adhesive and the like.

The adhesives are applied on the chassis 21, the leak-barrier sheets 24, the liquid-pervious sheets 34, 46, 47 and the liquid-impervious sheet 35 preferably in any one of spiral, wavy, zigzag, dotted or striped patterns. These chassis 21 and sheets 24, 34, 35, 46, 47 may be coated with adhesives in such patterns to define adhesive-coated regions and adhesive-free regions in these chassis 21 and sheets 24, 34, 35, 46, 47 and thereby to ensure these chassis 21 and sheets 24, 34, 35, 46, 47 are intermittently joined one to another, the cores 36, 48 are intermittently joined to the sheets 34, 35, 46, 47 and the elastic members 33, 65 are intermittently joined to the chassis 21 and sheet 24.

What is claimed is:

1. A disposable wearing article having longitudinal and transverse directions, said article comprising:
a liquid-impervious chassis comprising:
an inner surface,
a front waist region, a rear waist region, and a crotch region extending in the longitudinal direction between the front and rear waist regions,
front and rear ends respectively extending across said front and rear waist regions in said transverse direction, and
opposite lateral sections extending in said longitudinal direction between said front and rear ends;
a body fluid absorbent first panel having a front portion, a rear portion and opposite side edges, and being laid on the inner surface of said chassis so as to extend over said rear waist region and said crotch region of said chassis; and
a body fluid absorbent second panel having a proximal portion, a distal portion and opposite side edges, and being laid on the inner surface of said chassis so as to extend over said front waist region and said crotch region of said chassis;
wherein
said first panel is fixed at least at said front and rear portions to said chassis while said second panel being fixed at least at said proximal portion to said front waist region of said chassis;
said distal portion of the second panel extends over said crotch region of said chassis;
said opposite side edges of said first and second panels extend along the opposite lateral sections of said chassis;
said distal portion of said second panel is bent, along a bending zone contiguous to said proximal portion, upward at a predetermined angle with respect to said chassis so as to define an upward convex shape and to form between said chassis and said upwardly bent distal portion a pocket which opens toward said rear waist region;
said front end of said first panel extends into said pocket and terminates within said pocket at a location rearwardly spaced in the longitudinal direction from said bending zone of said second panel; and
said pocket is provided with a spacer extending in said transverse direction, said spacer having
transversely opposite ends joined to at least one of the transversely opposite lateral sections of said chassis and transversely opposite lateral portions of the distal portion of said second panel, and
an intermediate section defined between said transversely opposite ends, wherein the transversely opposite lateral sections of said distal portion are drawn by said spacer inward as viewed in said transverse direction of said chassis to keep the distal portion of the second panel in said upward convex shape and spaced upwardly from the intermediate section of the spacer.

2. The wearing article defined by claim 1, wherein the front portion of said first panel extends to at least a generally rear half of said crotch region while said distal portion of said second panel extends to a generally front half of said crotch region so that said front portion of said first panel underlies said distal portion of said second panel and extends into said pocket.

3. The wearing article defined by claim 1, wherein said spacer is elastically stretchable in the transverse direction and contractibly attached to the transversely opposite lateral sections of said distal portion so that the transversely opposite lateral sections of said distal portion are drawn inward as viewed in the transverse direction of said chassis under a contractile force of said spacer.

4. A disposable wearing article having longitudinal and transverse directions, said article comprising:
a liquid-impervious chassis having a front waist region, a rear waist region, and a crotch region extending in the longitudinal direction between said front and rear waist regions;
a body fluid absorbent first panel joined to an upper side of said chassis and extending in the longitudinal direction from said rear waist region towards said front waist region; and
a body fluid absorbent second panel comprising:
a front portion joined to the upper side of said chassis in said front waist region,
a rear portion extending obliquely upwardly from the upper side of said chassis and rearwardly in the longitudinal direction from said front portion towards said rear waist region, and
opposite upper and lower surfaces and an absorbent material between said upper and lower surfaces,
wherein the lower surface of said second panel in said rear portion is upwardly spaced from the upper side of said chassis to define a pocket between the lower surface of said second panel in said rear portion and the upper side of said chassis so that said second panel assumes an upward convex shape, said pocket being open rearwardly in the longitudinal direction towards said rear waist region; and
a spacer which is positioned in said pocket, extends in the transverse direction and comprises:
transversely opposite ends joined directly to transversely opposite sides of said rear portion of said second panel; and
an intermediate section between said transversely opposite ends and spaced upwardly from the upper side of said chassis and downwardly from the lower surface of said second panel in said rear portion;
wherein said spacer is elastically stretchable in the transverse direction and contractibly attached to said second panel so that said transversely opposite sides of said rear portion of said second panel are drawn inward in the transverse direction under contraction of said spacer to keep said rear portion of said second panel in said upward convex shape; and
wherein said first panel extends into said pocket and terminates within said pocket at a location rearwardly spaced in the longitudinal direction from said front portion of said second panel.

5. The wearing article defined by claim 4, wherein said spacer comprises
a water-pervious sheet; and
a plurality of stretchable elastic members elongated in the transverse direction, contractibly attached to said water-pervious sheet, and directly contacting the water-pervious sheet at multiple locations along an entire length, in the transverse direction, where the intermediate section is spaced upwardly from the upper side of said chassis and downwardly from the lower surface of said second panel in said rear portion.

6. The wearing article defined by claim 5, wherein
an entire dimension of the water-pervious sheet as measured in the transverse direction of the article is in a range of 20 to 93% of that of the second panel as measured in the transverse direction between transversely opposite side edges of the second panel.

7. The wearing article defined by claim 5, wherein
an entire dimension of the water-pervious sheet as measured in the transverse direction of the article is in a range of 50-80% of that of the second panel as measured in the transverse direction between transversely opposite side edges of the second panel.

8. The wearing article defined by claim 7, wherein
a tensile stress of the spacer in the transverse direction is in a range of 0.5 to 1.5N at a 100 to 250% stretched state.

9. The wearing article defined by claim 5, wherein
said water-pervious sheet is completely located within said pocket and has an entire dimension measured in the longitudinal direction of the article smaller than that of said pocket.

10. The wearing article defined by claim 9, wherein
a front end of said first panel extends into said pocket and underlies, while being downwardly spaced from, said rear end of said second panel; and
the entire dimension of said spacer as measured in the longitudinal direction of the article is smaller than that of the front end of said first panel underlying said rear end of said second panel.

11. The wearing article defined by claim 4, wherein
an entirety of the spacer is upwardly spaced from and free of direct contact with the first panel;
the transversely opposite ends of the spacer are joined directly to the transversely opposite sides of said rear portion of said second panel at locations which are upwardly spaced from an upper surface of a front end of the first panel, said front end being located within said pocket;
the intermediate section of the spacer is free of direct attachment to said first and second panels; and
said first panel further comprises an opposite lower surface joined to the upper side of said chassis.

12. The wearing article defined by claim 4, further comprising
a pair of liquid-impervious leak-barrier sheets between which said first and second panels are positioned, wherein each of said leak-barrier sheets has
a proximal section extending in the longitudinal direction along one of transversely opposite side edges of said chassis, said proximal section being attached to the upper side of said chassis; and
a distal section having a stretchable elastic member contractibly attached thereto so as to bias said distal section to rise above said chassis;
wherein the transversely opposite ends of said spacer are disposed between and bonded to the transversely opposite side edges of said chassis and the proximal sections of the respective leak-barrier sheets.

13. The wearing article defined by claim 11, wherein the locations where the transversely opposite ends of the spacer are joined directly to the transversely opposite sides of said rear portion of said second panel are located between and inwardly spaced, in the transverse direction, from further locations where transversely opposite side edges of the first and second panels are respectively joined together.

14. The wearing article defined by claim 5, wherein
an entirety of the spacer is upwardly spaced from and free of direct contact with the first panel;
the transversely opposite ends of the spacer are joined directly to the transversely opposite sides of said rear portion of said second panel at locations which are upwardly spaced from an upper surface of a front end of the first panel, said front end being located within said pocket;
the intermediate section of the spacer is free of direct attachment to said first and second panels; and
said first panel further comprises an opposite lower surface joined to the upper side of said chassis.

15. The wearing article defined by claim 14, wherein the locations where the transversely opposite ends of the spacer are joined directly to the transversely opposite sides of said rear portion of said second panel are located between and inwardly spaced, in the transverse direction, from further locations where transversely opposite side edges of the first and second panels are respectively joined together.

* * * * *